US008356896B2

(12) United States Patent
Esser et al.

(10) Patent No.: US 8,356,896 B2
(45) Date of Patent: Jan. 22, 2013

(54) METHOD FOR DETERMINING FAR AND NEAR REFERENCE POINTS

(75) Inventors: Gregor Esser, Munich (DE); Nadine Jung, Munich (DE); Katrin Nicke, Neuried (DE); Ilka Schwarz, Geretsried (DE); Andrea Welk, Munich (DE); Martin Zimmerman, Erdweg-Kleinberghofen (DE)

(73) Assignee: Rodenstock GmbH, Munich (DE)

( * ) Notice: Subject to any disclaimer, the term of this patent is extended or adjusted under 35 U.S.C. 154(b) by 511 days.

(21) Appl. No.: 12/524,314

(22) PCT Filed: Jan. 25, 2008

(86) PCT No.: PCT/EP2008/000587
§ 371 (c)(1),
(2), (4) Date: Mar. 10, 2010

(87) PCT Pub. No.: WO2008/089998
PCT Pub. Date: Jul. 31, 2008

(65) Prior Publication Data
US 2010/0296055 A1 Nov. 25, 2010

(30) Foreign Application Priority Data
Jan. 25, 2007 (DE) .......................... 10 2007 003 845

(51) Int. Cl.
*A61B 3/10* (2006.01)
*A61B 3/00* (2006.01)
*A61B 3/14* (2006.01)
*A61B 3/02* (2006.01)

(52) U.S. Cl. ........ 351/204; 351/200; 351/210; 351/222; 351/246

(58) Field of Classification Search ................... 351/204, 351/200, 205–206, 209, 210, 218, 221–223, 351/227–228, 246, 41
See application file for complete search history.

(56) References Cited

U.S. PATENT DOCUMENTS

| 5,617,155 | A | 4/1997 | Ducarouge et al. |
| 5,984,473 | A * | 11/1999 | Livnat ........................... 351/177 |
| 6,089,713 | A | 7/2000 | Hof et al. |
| 7,837,325 | B2 * | 11/2010 | Wooley et al. ................. 351/177 |

(Continued)

FOREIGN PATENT DOCUMENTS

| DE | 197 01 312 A1 | 7/1998 |
| DE | 103 13 275 A1 | 10/2001 |

(Continued)

OTHER PUBLICATIONS

Dipl-Ing. Stefanie Schuldt, "ysis-Natuerliches Sehen erleben", XP-002398937, May 2004, pp. 38-43.
"ImpressionIST—Das 4-in-1 Integrierte Service-Terminal von Rodenstock", XP-000962763, Jan. 2006, pp. 56-61.
Communication referred to in Article 94(3) EPC dated Nov. 16, 2011 (Five (5) pages).

(Continued)

*Primary Examiner* — Dawayne A Pinkney
(74) *Attorney, Agent, or Firm* — Crowell & Moring LLP

(57) ABSTRACT

The invention relates to a method for specifying or determining the spatial position of a distance reference point and/or a near reference point of a progressive spectacle lens for correcting defective vision of a spectacle wearer. Said method consists of the following steps: individual data of the spectacle wearer is obtained; the individual vertical and/or the horizontal position of the distance reference point and/or the near reference point is determined or calculated in accordance with the determined individual data of the spectacle wearer.

23 Claims, 18 Drawing Sheets

U.S. PATENT DOCUMENTS

| | | |
|---|---|---|
| 2007/0132945 A1 | 6/2007 | Haser et al. |
| 2009/0021693 A1 | 1/2009 | Sessner et al. |

FOREIGN PATENT DOCUMENTS

| | | |
|---|---|---|
| DE | 10 2005 003 699 A1 | 7/2006 |
| EP | 0 562 336 A | 9/1993 |
| WO | WO0157584 | 8/2001 |
| WO | WO 01/81979 A2 | 11/2001 |
| WO | WO 2005/029160 A1 | 3/2005 |

OTHER PUBLICATIONS

Guth O, "Gradal Individual Framefitt-Die Neue Gestaltungsfreihei Bei Gleitsichtglasern", Deutsche Optikerzeitung, Opt. Fachveroeff, Jun. 1, 2005, pp. 76-80, XP000962819.

Gregor Esser, "Die Performance individueller Gleitschtglaeser", Deutsche Optiker Zeitung, Dec. 1, 2005, pp. 38-44, XP000962762.

International Search Report including partial translation dated Jun. 10, 2008 (Seventeen (17) pages).

* cited by examiner

FIG 2

Ordered values (22)

|   | Sph | Cyl | Axis | Add | Prism | Base | Coating (28) | Color (30) |
|---|---|---|---|---|---|---|---|---|
| R | -1 | -2 | 0 | 2 | | | | |
| L | -0,5 | -0,25 | 45 | 2 | | | | |

Individual parameters (24)

|   | PD [mm] | CVD [mm] | FI [°] | FFA [°] | Base curve [D] (34) |
|---|---|---|---|---|---|
| R | 34,1 | 11,8 | 8,1 | 4 | 4 |
| L | 33 | 11,2 | 8,9 | | (desired or support disk value) |

Frame and centration data (26)

|   | Fitting height [mm] | u [mm] | v [mm] | | | |
|---|---|---|---|---|---|---|
| | | | | Horizontal lens size | 51,5 | [mm] |
| | | | | Vertical lens size | 31,1 | [mm] |
| R | 20,5 | 0,3 | 5 | AzG | 17,5 | [mm] |
| L | 18,9 | 1,5 | 3,3 | | | |

Centration dimensions (27)

L  R
15,2  18,0  14,0

| Frame from tracer ○ | Frame Rodenstock ○ | Zoom ○ |
| | Approximate shapes ○ | |

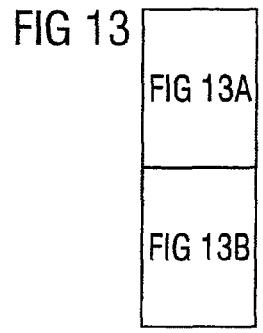

FIG 13A

Rodenstock spectacle lenses    ○ Order    ○ Request    ○ Repetition

| Order basic data | Customer no.: _____  Comission: _____ | Company |
|---|---|---|
| | Date: _____  Delivery: _____ | |
| | Lens type / EDP code: _____ R⌀___ / ___ ○ centr. | |
| | Color / Coating: _____ L⌀___ / ___ ○ centr. | |

| | Sph. | Cyl. | Axis | Add | Prism 1 | Base 1 | Prism 2 | Base 2 |
|---|---|---|---|---|---|---|---|---|
| R | | | | | | | | |
| L | | | | | | | | |

Adjustment of prismatic vertical differences in case of anisometropy ○ yes ○ no

Allocate prisms?
R/L
○ yes
○ no

Frame and centration data

| Frame [Box dimension in mm] | | | Centration fitting data in mm | | | Centration correction taken into account ○ yes ○ no |
|---|---|---|---|---|---|---|
| HLS | VLS | AzG | Horizontal | $P_R$ | $P_L$ | |
| | | | Vertical | $Y_R$ | $Y_L$ | |

R    L

Draw in drill holes and nicks

| ○ MDM ○ Optimized diameter | Min. edge thickness of the edged lens [mm] | Thickness at marked point [mm] |
|---|---|---|

FIG 13B

| | | | |
|---|---|---|---|
| Optimization parameters | Pupillary distance (PD) [mm] | R | L |
| | CVD of the correction spectacles [mm] | R | L |
| | CVD of the measurement spectacles [mm] | R | L |
| | Frame forward inclination [°] | R | L |
| | Face form angle [°] | R | L |
| | Inset [°] | R | L |

○ Standard Design    ○ Frame - optimized design    ○ Individual design
  ○ DN=-18 mm      please indicate frame and      Design point distance: (DD):___
  ○ DN=-16 mm      centration data      Design point near: (DN):___
  ○ DN=-14 mm
○ Individual near distance
  Refraction distance NEAR _____ cm      ○ Base curve ____ D
  Principal viewing distance NEAR ____ cm

| | | | | | | | | | | | |
|---|---|---|---|---|---|---|---|---|---|---|---|
| Prisms | For prisms in position of wear | | | | | | | | | | |
| | Arrangement of the refraction lenses in the measurement spectacles (perpendicular in front of the eye) | | | | | | | | | | |
| | | Sph. | Cyl. | Prism | Base | Slant | Eye | Sph. | Cyl. | Prism | Base | Slant |
| | 5 | | | | | | | | | | | |
| | 4 | | | | | | Frame | | | | | |
| | 1 | | | | | | Plane | | | | | |
| | 2 | | | | | | | | | | | |
| | 3 | | | | | | Object | | | | | |
| | Centration of the refraction lenses in the measurement spectacles | | | | | | | | | | |
| | ○ PMZ | ○ Formula centration | ○ Special case | | | Horizontal [mm] | R | L | | | |
| | | | | | | Vertical [mm] | R | L | | | |
| | Position of the facette | | | | | | | | | | |
| | Expected facette course of the edged lens | | | R ○ Object-side   ○ 1/2 Eye-side   ○ 1/3 Eye-side | | | | | | | |
| | | | | L ○ Object-side   ○ 1/2 Eye-side   ○ 1/3 Eye-side | | | | | | | |

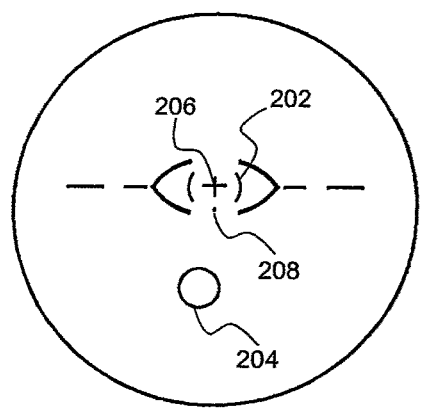 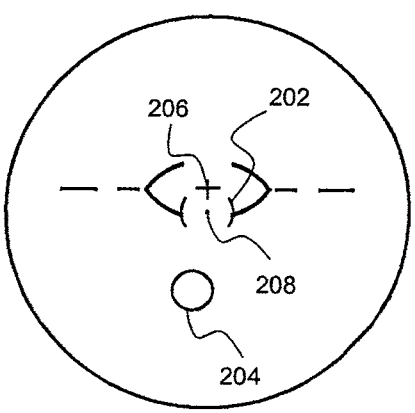
Fig. 16a  Fig. 16b
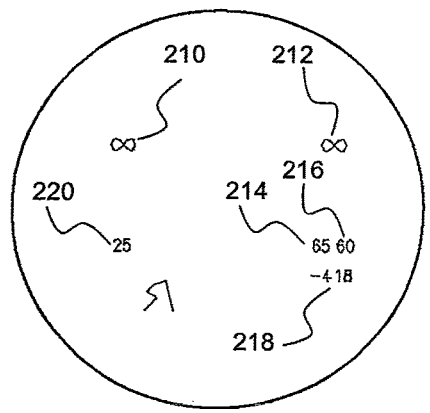
Fig. 17

FIG 18
Impression FreeSign Perfalit 1.6
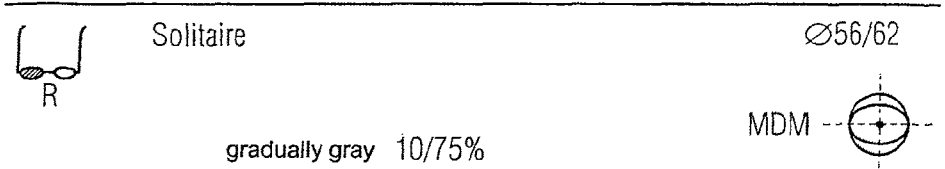
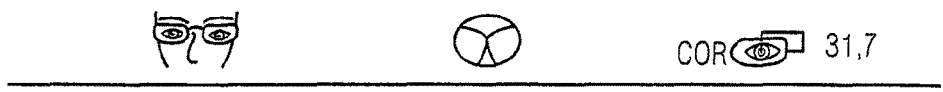
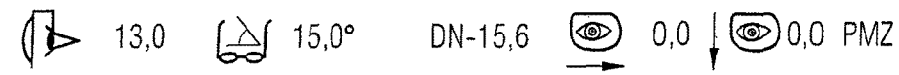

FIG 19

| | prescription values | | |
|---|---|---|---|
| ◡◡ | right | △ | prism |
| ◡◡ | left | ⊕ | base |
| ⊕ | sphere | ✚ | sphere |
| ⬚ | cylinder | ▤ | prescription value |
| ⌒ | axis | ≡◁ | target value |
| ∅ | diameter | ⊙ | center thickness minimization |
| individual parameters | | design parameters | |
| ▱ | corneal vertex distance | DF | design point distance |
| ▱ | face form angle | DN | design point near |
| ▱ | forward inclination | BC | base curve |
| ◉ | pupillary distance right | INS | inset |
| ◉ | pupillary distance left | | |
| centration | | | |
| COR◉ | corrected fitting PD right | COR◉ | corrected fitting PD left |
| ◉→ | centration correction right nasal | ←◉ | centration correction left nasal |
| ←◉ | centration correction right temporal | ◉→ | centration correction left temporal |
| ↓◉ | centration correction right bottom | ↓◉ | centration correction left bottom |
| ↑◉ | centration correction right top | ↑◉ | centration correction left top |
| PMZ | pupil center centration | FF | formula centration |
| additional information | | | |
| CVD Refraktion | Corneal vertex distance refraction | HDEC | horizontal predecentration |
| Prism Adaption | prism adaption | MVDN | main visual distance near |
| RDN | refraction distance near | | |

METHOD FOR DETERMINING FAR AND NEAR REFERENCE POINTS

BACKGROUND AND SUMMARY OF THE INVENTION

The invention relates to a method for specifying or determining the spatial position of a distance and/or a near reference point of a progressive spectacle lens, as well as a corresponding apparatus, a computer program product, a storage medium, and a graphical user interface. Furthermore, the invention relates to a method for determining or calculating an individual spectacle lens design as well as to a corresponding apparatus, a computer program product, a storage medium, and a graphical user interface.

Individual spectacle lenses, in particular progressive individual spectacle lenses, have been described in numerous patent publications (for example DE 197 01 312, DE 103 13 275, WO 01/81979). These lenses exhibit clearly better imaging properties than conventional spectacle lenses, since the individual situation of wear of the spectacle wearer is taken into account in the calculation or optimization.

Calculation or optimization of spectacle lenses and in particular of progressive spectacle lenses in the respective position of wear and situation of wear have achieved a high technical and optical standard since. For example, according to the prior art, progressive spectacle lenses can be optimized and calculated online after receipt of order, taking into account the individual prescription (sph, cyl, axis, add, prism, base) and the individual positions of the lenses in front of the eyes of the spectacle wearer (corneal vertex distance CVD, face form angle FFA, forward inclination FI, pupillary distance).

It is the object of the invention to improve the optimization of individual progressive spectacle lenses.

This object is solved by a method for specifying or determining the spatial position of a distance and/or a near reference point of a progressive spectacle lens with the features according to claim 1, a computer program product with the features according to claim 14, a storage medium with the features according to claim 15, an apparatus for determining the spatial position of a distance and/or a near reference point with the features according to claim 16, as well as a graphical user interface with the features according to claim 17. Furthermore, the object is solved by a method for determining or calculating an individual spectacle lens design with the features according to claim 20, a computer program product with the features according to claim 23, a storage medium with the features according to claim 24, an apparatus with the features according to claim 25, as well as a graphical user interface with the features according to claim 26. Preferred embodiments are subject of the dependent claims.

According to the invention, a computer-implemented method for specifying or determining the spatial position of a distance and/or a near reference point of the progressive spectacle lens for correction of a visual defect of a spectacle wearer is provided, wherein the method comprises the following steps:

obtaining individual data of the spectacle wearer;
determining or calculating the individual vertical and/or the horizontal position of the distance and/or the near reference point depending on the collected individual data of the spectacle wearer.

In progressive spectacle lenses, there are four marked points on the spectacle lens, which can be reconstructed at any time by means of at least one permanent marking on or in the spectacle lens and a predetermined reconstruction rule of these four points relative to the permanent marking (cf. for example EN ISO 8989-2). These points are described in the standard (EN ISO 13666) and e.g. in "Handbuch für Augenoptik", Zeiss, Vol. 4 2000, page 117. The spatial positions of the reference points are usually also marked by means of a non-permanent marking (e.g. stamping) of the spectacle lens (cf. EN ISO 13 666 and DIN 58 208 part 2).

The distance reference point is defined as that point on the front surface in which the predetermined distance power is to be, in fact preferably in that ray path that is in front of the eye when the spectacle lens is in use.

The near reference point is defined as that point on the front surface in which the predetermined near power is to be, in fact in that ray path that is in front of the eye when the spectacle lens is in use.

The prism reference point is defined as that point on the front surface indicated by the manufacturer, in which the prismatic powers of the finished lens are to be determined.

The centration point is defined as that point with which the fitting point is to coincide, wherein the fitting point is a point on the front surface of a progressive spectacle lens, which according to the manufacturer is to serve as a reference point for the positioning of the spectacle lens in front of the eye.

According to the conventional methods for producing spectacle lenses and in particular progressive spectacle lenses, the positions of the reference points, in particular the distance and near reference points, are fixedly set for the respective spectacle lens by the manufacturers. These positions are largely independent of the individual data of the spectacle wearer, i.e. the positions of the reference points are not selected and specified depending on individual data of the respective spectacle wearer.

The centration of the finished spectacle lenses in the spectacle frame may take place according to different spectacle centration requirements:

1. field of sight requirement
2. center of rotation requirement
3. reference point requirement The centration of spectacle lenses is explained in detail for example in the book "Optik and Technik der Brille", H. Diepes and R. Blendowske, 2002, Optische Fachveröffentlichung GmbH, Heidelberg, page 308, which is explicitly referred to for the sake of explanation of all terms not defined herein any further.

For the centration of a progressive spectacle lens, in particular the field of sight requirement and the reference point requirement are of importance.

The field of sight requirement states that the fields of sight of both eyes are congruent in a habitual head and body posture in the desired object distance. The progressive lens is centered in such a manner that with a normal, habitual head and body posture and a straight sight (zero direction of sight), the centration point lies in front of the pupil center. Thereby, it is achieved that the field of sight requirement is usually met.

The reference point requirement states that the reference point is to coincide with the main visual point of the two eyes. The main directions of sight of the spectacle wearer are inherent and individual properties of the spectacle wearer, while the reference points are specified on the spectacle lens.

According to the invention, it has been particularly found out that with the conventional production methods for progressive lenses with (not individually) specified positions of distance and near reference points, the reference point requirement is usually not met, which leads to a deterioration of the imaging properties of the spectacle lens or the spectacles, as well as fatigue and incompatibility. In particular, according to the invention, it has been found out that for progressive lenses produced according to conventional methods with specified reference points, the reference point requirement is only met if the main directions of sight for distance and near of the spectacle wearer are purely by accident coincident with the reference points on the spectacle lens stipulated by the manufacturer. In a number of cases, however, the main directions of sight and the location of the distance and near reference points do no coincide. For example, if the distance reference point is 4 mm above the centration point and the near reference point is 18 mm below the centration point (standard values in conventional spectacle lenses), the main direction of sight "distance" would have to be approx. 8 degrees above the zero direction of sight, and the main direction of sight "near" would have to be approx. 36 degrees below the zero direction of sight. However, if the individual main directions of sight deviate from those, the reference points requirement can no longer be met and the spectacle wearer has to adjust their main directions of sight to the spectacle lens.

The invention breaks with the conventional procedure according to which the spatial position, in particular the vertical location, of the reference points is specified. Instead, it is suggested to vary the spatial positions, in particular the vertical positions, of the distance and near reference points freely (within certain limits) depending on the individual data of the spectacle wearer, and to specify them specifically for the respective, individual spectacle wearer.

After the optimum individual position of the distance and/or the near reference point has been determined, the spectacle lens is optimized such that the predetermined distance and near portion powers required for the spectacle wearer are achieved in the thus specified, individual reference points for "distance and near". Here, the power preferably refers to the power of wear, i.e. the power of the spectacle lens in the position of wear. The position of the individually determined distance and/or near reference point(s) is taken into account in the calculation or optimization of the individual spectacle lens design or individual spectacle lens as design parameters. The individually specifiable distance and near reference points are therefore referred to as design point "distance" and design point "near", respectively, in the following.

In particular, the individually determined distance reference point or design point "distance" corresponds to the point by which the spectacle wearer is optimally corrected in their distance vision and which corresponds to the personal viewing habits of the spectacle wearer. The individually determined near reference point or design point "near" corresponds to the point by which the spectacle wearer is optimally corrected in their near vision tasks and can lower their views in a way comfortable to them.

By means of the inventive method, it can be ensured that the distance and near reference points or design point "distance" and "near" of a spectacle lens optimized and produced according to the invention and the main directions of sight of the spectacle wearer coincide.

The possibility to freely select the position of the distance and/or the near reference point within certain limits represents a significant, additional degree of freedom in the determination of the individual design of the spectacle lens. Thus, the location, in particular the vertical position, and optionally the size of the viewing zones (distance, near and intermediate or progression zone) can be selected freely and individually within certain limits and be optimally adapted to the respective individual wearer situation. Since the distance and the near reference points of the spectacle lens can be optimally adapted to the main directions of sight of the spectacle wearer, it is possible to obtain optimum viewing zones tailored to vision needs and thus an optimum viewing comfort with the spectacle lens. Furthermore, the eyes and the cervical spine are relieved and eye fatigue is reduced.

As explained above, the spatial positions of the individually determined distance and/or near reference point(s) as well as the fitting point are for example marked by means of a non-permanent marking (e.g. stamping) of the finished individual spectacle lens. The positions of the individually determined distance and near reference portions and the centration or fitting point can also be uniquely reconstructed by means of suitable reconstruction rules (individual templates, centration cards, etc.) assigned to the individual spectacle lens on the basis of the permanent markings of the spectacle lens (cf. EN ISO 8989-2, item 7.1). Thus, the positions of the distance and near reference points and the centration or fitting point can be uniquely reconstructed on the basis of permanent markings of the spectacle lens. According to an aspect of the invention, the system comprising a preferred individual spectacle lens, in particular produced by means of a preferred inventive method and an individual reconstruction rule assigned to the spectacle lens, is protected.

The individual data of the spectacle wearer, which is taken into account in the determination of the spatial position, in particular of the vertical position of the distance and/or the near reference point, comprises one or more of the following data or sets of data:

refraction data or power parameters, in particular sphere, cylinder, axis position, addition; and/or individual parameters of the spectacle wearer and the individual position of wear of the spectacle lens or the spectacles in front of the eyes of the spectacle wearer. The individual parameters comprise in particular the pupillary distance, the corneal vertex distance (CVD), forward inclination (FI), face form angle (FFA), etc.; and/or data relating to the preferences or the weighting of the distance, the near and the intermediate or progression zone of the progressive spectacle lens; and/or data relating to the spectacle lens worn so far, in particular as to whether the previous spectacle lens is a single-vision, bifocal or progressive spectacle lens, data relating to the design (hard/soft), the progression length, the type (individual, conventional), the material (plastics/silicate), the refractive index, the location of the reference points, the addition of the previous spectacle lenses, and/or the change of the refraction data in comparison to the refraction data of the previous spectacle lens, and/or data relating to the desired improvements with respect to the so-far worn spectacles, in particular larger distant zone, larger intermediate zone, larger near zone, fewer infraduction when reading, or reduced rocking motion; and/or data relating to the main use of the spectacle lens (driving, computer work place, reading, crafts, etc.); and/or data relating to the environmental influences (brightness of the surrounding, etc.); and/or data relating to the main direction of sight in distance and near;

data relating to potentially present, individual, exceptional head and body postures; and/or frame and centration data, in particular vertical lens size and centration height, frame shape; distance between the lenses, corrected PD for fitting (CorPD); and/or physiological parameters, in particular of the eye or the eyes of the spectacle wearer, in particular visus with correction, stereopsis; and/or data relating to the individual object distances, in particular working distance when reading (near work), working distance in the distance; and/or data relating to the object distances in the refraction determination: "distance" and "near".

Moreover, the individual data of the spectacle wearer may comprise further individual parameters.

The individual data of the spectacle wearer is collected, evaluated and control or determine the spatial position of the individual distance and/or near reference point(s).

Preferably, the vertical distance of the distance and near reference points from a predetermined or predeterminable centration or fitting point of the spectacle lens is specified depending on the individual data of the spectacle wearer. The method for specifying or determining the spatial position of a distance and/or a near reference point preferably comprises a step of specifying the position of the centration or fitting point.

Preferably:
the vertical height of the distance reference point, measured from the centration or fitting point of the spectacle lens, can be set to a value of −4 mm below up to 4 mm above the centration or fitting point, preferably in steps of 0.1 mm, depending on the individual data of the spectacle wearer; and/or
the vertical height of the near reference point, measured from the centration point of the spectacle lens, can be set to a value of −13 mm to −20 mm below the centration or fitting point, preferably in steps of 0.1 mm, depending on the individual data of the spectacle wearer.

The vertical direction preferably relates to the vertical direction in the position of wear of the spectacle lens, wherein the spectacle lens is e.g. located in an average (e.g. as defined in DIN 58 208 part 2) or in an individual position of wear. Preferably, the spectacle lens is arranged in an individual position of wear. The coordinate system is preferably a Cartesian coordinate system in the object-side surface of the spectacle lens, wherein the origin of the coordinate system coincides with the centration or fitting point of the spectacle lens. The vertical and horizontal axes lie in the tangential plane with respect to the object-side surface in the geometric center or the centration or fitting point.

Furthermore, the distance between the vertical heights of the distance and near reference points (i.e. the progression zone length) is preferably larger than or equal to 13 mm. Further preferably, the near reference point is located at least 2 mm above the lower frame edge and/or the distance reference point is located at least 8 mm below the upper frame edge.

For example, the positions of the individual distance and near reference points may be indicated by the optician/optometrist directly when placing the order. Preferably, however, the optimum position of the distance and/or the near reference point is automatically calculated from the individual data of the spectacle wearer with the aid of a computer.

Preferably, the individual data of the spectacle wearer comprises data relating to the preferences or the weighting of the distance, near and/or the progression zone. Preferably it follows that:
for the vertical distance $y_{BF}$ of the distance reference point from the centration or fitting point of the spectacle lens $y_{BF}=4-4*G_F/33.33$ [mm] for $0 \leq G_F < 33$ and $y_{BF}=0-4*(G_F-33.33)/66.66$ [mm] for $33 \leq G_F \leq 100$, and/or
for the vertical distance $y_{BN}$ of the near reference point from the centration or fitting point $y_{BN}=-20+2*2G_N/33$ [mm] for $0 \leq G_N < 33$ and $y_{BN}=-18+5*(G_N-33.33)/66.66$ [mm] for $33 \leq G_N \leq 100$;

wherein $G_F$ designates the weighting of the distance zone and $G_N$ designates the weighting of the near zone.

According to a further embodiment, the vertical distance $y_{BF}$ of the distance reference point from the centration or fitting point indicated for this spectacle lens and the vertical distance $y_{BN}$ of the near reference point from the centration or fitting point may be calculated according to the following formulas:

$y_{BF}=(GW1*y_{BF1}+y_{BF2})/(g_1)$ $y_{BN}=(GW2*y_{BN1}+y_{BN2})/(g_2)$ wherein $y_{BF1}=4-4*G_F/33.33$ [mm] for $0 \leq G_F < 33$ and $y_{BF1}=0-4*(G_F-33.33)/66.66$ [mm] for $33 \leq G_F \leq 100$;

$y_{BN1}-20+2*2G_N/33$ [mm] for $0 \leq G_N < 33$ and $y_{BN1}=18+5*(G_N-33.33)/66.66$ [mm] for $33 \leq G_N \leq 100$;

$y_{BF2}=y_{BN1}+y_P$ $y_{BN2}=y_{BF1}-y_P$ $y_P=13+5*G_P/33.33$ [mm] for $0 \leq G_P < 33$ and $y_P=18+2*(G_P-33.33)/66.66$ [mm] for $33 \leq G_P \leq 100$;

wherein:
the coefficients GW1 and GW2 assume values between 1 and 2, and wherein
$G_F$ designates the weighting of the distance zone;
$G_N$ designates the weighting of the near zone; and
$G_P$ designates the weighting of the intermediate or progression zone
$g_1=1+GW1$
$g_2=1+GW2$.

Preferably, the individual data of the spectacle wearer comprises individual parameters of the eyes of the spectacle wearer and/or of the arrangement of the spectacles in front of the eyes of the spectacle wearer.

In particular, the individual parameters of the eyes of the spectacle wearer and/or the arrangement of the spectacles in front of the eyes of the spectacle wearer comprise the pupillary distance, the corneal vertex distance, the forward inclination, the face form angle, etc.

The spatial position, in particular the vertical distance of the distance and/or the near reference point from the centration point, depends particularly on the forward inclination and the corneal vertex distance. The standard value or the value underlying a standard or basic design is e.g. 9 degrees for the forward inclination and 13 mm for the corneal vertex distance. If the actual values (CVD and forward inclination) deviate therefrom, the vertical positions of the reference points are adapted accordingly according to the invention, in order to avoid e.g. extremely high sight deviations, or eye excursions, in near vision with low CVD values.

This may be done e.g. by means of the following formula:

$y_{Bnew}=y_{Bold}*(CVD+13.5$ mm$)/26.5$ mm$*$cosine(forward inclination)/cosine(9 degrees), wherein:
$y_{Bnew}$ designates the new vertical position of the distance and/or the near reference point;
$y_{Bold}$ designates the vertical position of the distance and/or the near reference point according to the standard design.

Further preferably, the individual data of the spectacle wearer comprises data relating to
the individual object distance for distance and/or the individual object distance for near; and/or
the individual object distance for distance in the refraction determination and/or the individual object distance for near in the refraction determination.

Preferably, the individual data of the spectacle wearer comprises:
- data relating to spectacles worn so far; and/or
- data relating to desired improvements of the spectacles worn so far.

Further preferably, the individual data of the spectacle wearer comprises:
- data relating to the individual main direction of sight for distance and closes-up; and/or
- data relating to the individual head and body posture; and/or
- physiological parameters, in particular of the eye of the spectacle wearer; and/or
- preferences or a weighting of the importance of the imaging properties as against the aesthetic properties of the spectacle lens.

According to a further preferred embodiment of the inventive method, the individual data of the spectacle wearer comprises data in at least two different categories of the individual data and the determination of the position of the distance and/or the near reference point comprises the following steps:
- determining an ideal position of the distance reference point and/or an ideal position of the near reference point for each of the categories on the basis of individual data of the spectacle wearer in the respective category;
- calculating the position of the distance reference point and/or the position of the near reference point on the basis of the determined ideal position of the distance and/or the near reference point in the respective categories.

Preferably, the position of the distance and/or the near reference point is calculated according to the formula:

$$y_{DF,DN} = \sum_{i=1}^{N} g_i y^i_{DF,DN}$$

$$\sum_{i=1}^{N} g_i = 1$$

wherein:

$g_i$ designates the weighting of the $i^{th}$ category;

$y_{DF,DN}^i$ designates the ideal position of the distance reference point DF and the near reference point DN, respectively, for the $i^{th}$ category; and N designates the number of different categories.

Preferably, the inventive method further comprises the steps of
- calculating an individual spectacle lens design exhibiting the individually specified distance and/or near reference point(s);
- visualizing the calculated, individual spectacle lens design and the spatial position of the individual distance and/or near reference point(s).

Furthermore, according to the invention, a computer program product and a storage medium with a computer program stored thereon are provided, wherein the computer program is adapted, when loaded and executed on a computer, to perform the inventive method for specifying or determining the individual spatial position of a distance and/or a near reference point of a progressive spectacle lens.

Furthermore, according to the invention, an apparatus for determining the individual spatial position of a distance and/or a near reference point of a progressive spectacle lens is provided, comprising:

- obtaining means for obtaining individual data of the spectacle wearer;
- calculating or optimizing means adapted to perform a preferred inventive method for determining the spatial position of the distance and/or the near reference point depending on the collected individual data of the spectacle wearer.

Furthermore, according to the invention, a graphical user interface for specifying or determining and presenting, or displaying, the spatial position of an individual distance and/or near point of a progressive spectacle lens is provided, comprising
- at least one individual data input portion adapted to input individual data of the spectacle wearer; and
- at least one display portion adapted to present the spatial position of the distance and/or the near reference point, wherein the spatial position of the distance and/or the near reference point is determined according to a preferred inventive method depending on the individual data of the spectacle wearer.

Preferably, the display portion is further adapted to present an individual spectacle lens design, wherein the individual spectacle lens design exhibits the individually set distance and/or near reference point(s).

Preferably, the graphical user interface comprises a tuning or adaptation portion adapted to perform an adaptation of the vertical and/or the horizontal position of the distance and/or the near reference point and/or an adaptation of at least part of the individual parameters of the spectacle wearer.

Furthermore, according to the invention, a computer-implemented method for determining or calculating an individual spectacle lens design for a progressive spectacle lens for correction of a visual defect of a specific spectacle wearer is proposed, comprising the following steps:
- obtaining individual data of the spectacle wearer;
- determining or calculating the spatial position of a distance and/or a near reference point depending on the collected individual data of the spectacle wearer, according to a preferred inventive method;
- calculating the spatial position and/or the size of a distance, a near and a progression zone of the spectacle lens design depending on the determined individual spatial position of the distance and/or the near reference point.

A design of a spectacle lens comprises in particular the spatial distribution of the target values across the spectacle lens for one or more aberrations taken into account as target values in the optimization of the spectacle lens. In particular, a spectacle lens design is characterized by the distribution of the refraction error (i.e. the difference of the refractive power of the spectacle lens and the refractive power determined by means of refraction determination) and/or the distribution of the astigmatism error or the astigmatic deviation (i.e. the difference of the astigmatism of the spectacle lens and the astigmatism determined by means of refraction determination). Furthermore, a spectacle lens design may also comprise the distribution of the target values for magnification, distortion errors or other aberrations, which may be surface values or preferably values of wear, i.e. values in the position of wear of the spectacle lens. Moreover, the spectacle lens design may comprise a suitable object model. The object model may for example comprise an object distance function defined as the reciprocal object distance along the principal line. An example of a suitable object model is defined in DIN 58208 part 2 (cf. image 6). Likewise, a standardized position of wear is defined in DIN 58 208 part 2.

A design comprises a predetermined spatial position of the distance and/or the near reference point if the distance and/or the near portion power (which is determined for example by means of refraction) prescribed and required for the spectacle wearer is achieved in the respective reference point. Put differently, the aberrations (in particular astigmatic deviation and refractive error) associated to the design are to be as small as possible (preferably substantially zero) in the distance and/or the near reference point.

In order to produce progressive lenses with different designs, i.e. with different target values for the aberrations (in particular target values for the spatial distribution of the astigmatic deviation and/or the refraction error) for example caused by different positions of the distance and/or the near reference point, the corresponding different design or target values have to be created and optimization has to be performed therewith. The calculation of an individual spectacle lens design as defined by this application consequently comprises calculating the target values for the individual aberrations, which are to be attributed to the individual spectacle lens design, in particular the target values for the astigmatic deviation and/or the refraction error.

A progressive spectacle design usually comprises a distance, a near and an intermediate or progression zone. The 0.5 D astigmatism line is usually used for delimiting the individual viewing zones from the periphery. However, it is possible to use other isoastigmatism lines, such as the 0.75 or 1.0 D isoastigmatism lines, for delimiting the viewing zones. Accordingly, the viewing zones comprise the surface between the temporal and the nasal isoastigmatism line, preferably between the nasal and the temporal 0.5 D isoastigmatism line. In the horizontal direction, the viewing zones are consequently delimited from the periphery by the nasal and temporal isoastigmatism lines (e.g. 0.5 D isoastigmatism line).

The horizontal line $(x, y=y_{FP})$, which passes through the point $(x_{FP}, y_{FP})$ on the principal line in which a refractive power increase of 15% of the addition is achieved, may for example serve for delimiting the progression zone from the distance zone in the vertical direction. All points on or above the horizontal line $(x, y=y_{FP})$ which have a target astigmatism $\leq 0.5$ D may thus be attributed to the distance zone.

The horizontal line $(x, y=y_{NP})$, which passes through the point $(X_{NP}, Y_{NP})$ on the principal line in which a refractive power increase of 85% of the addition is achieved, may serve to delimit the progression zone from the near zone in the vertical direction. All points on or below the horizontal line $(x, y=y_{NP})$ which have a target astigmatism of $\leq 0.5$ D may thus be attributed to the near zone.

All points $(x, y)$ between the two horizontal lines $(x, y=y_{FP})$ and $(x, y=y_{NP})$, which have a target astigmatism of $\leq 0.5$ D, are attributed to the progression zone. Of course, the viewing zones may be horizontally delimited from each other in a different, suitable manner.

The refractive power increase in a point on the principal line is the difference of the target refractive power in this point and the refractive power in the distance reference point. The addition is defined as the difference between the target refractive powers in the distance and near reference points.

The coordinate system preferably relates to the above-defined coordinate system.

Accordingly, the calculation of a spectacle lens design comprises in particular determining the spatial position (in particular the vertical and/or the horizontal position) as well as optionally the size of the viewing zones of the spectacle lens (i.e. the distance, the near and the intermediate or progression zone) depending on the determined individual, spatial position of the distance and/or the near reference point. The spatial position of the viewing zones is in particular predetermined by the spatial position of the distance and near reference point(s). The size of the viewing zones is preferably calculated automatically from the default values for the spatial position of the distance and near reference points.

In this context, the size of the respective viewing zone is in particular understood to be the area of the respective viewing zone. The spatial position of the respective viewing zone is in particular understood to be the area centroid of the respective viewing zone.

The spectacle lens design variably dependent on the variable position of the (individual) distance and/or the near reference point can be recalculated each time for each position of the distance and/or the near reference point. Alternatively, for each combination of the positions of the distance and/or the near reference point, preferably taking into account individual parameters of the eyes of the spectacle wearer and/or the individual situation of wear, individual spectacle lens designs may be calculated in advance and stored for example in a database. Preferably, however, the calculation of the individual spectacle lens design with variable position of the distance and/or the near reference point is performed by means of a transformation of a predetermined base or starting design.

A method for calculating an individual design by means of a transformation of a predetermined base or starting design is for example described in the German patent application DE 10 2007 003 849.

Preferably, the spectacle lens design is calculated by means of the transformation (e.g. a suitable stretching or compression, or squeezing) of a predetermined base or starting design, wherein the transformation is a function of the vertical and/or the horizontal spatial position of the specified distance and/or near reference point(s).

Preferably, the target values $S(y)$ for the spatial distribution of at least one aberration (for example the astigmatic error) of the individual spectacle lens may be calculated by means of a mapping $S(y')=S'(y')$ and a transform $Y: y \mapsto y', y \mapsto y'(y)=y-\Delta y(y)$ of a corresponding target value $S'(y')$ of the base or starting design, wherein y' is the vertical coordinate of the target value of the starting design and y is the vertical coordinate of the transformed target value of the individual spectacle lens design.

The vertical direction preferably relates to the vertical direction in the position of wear of the spectacle lens, wherein the spectacle lens is e.g. arranged in an average (e.g. as defined in DIN 58 208 part 2) or in an individual position of wear. Preferably, the spectacle lens is located in an individual position of wear. The coordinate system preferably is the above-defined coordinate system. Of course, it is possible to define the transformation in other suitable coordinate systems.

In the simplest case, the transformation Y may be of the form $\Delta y(y)=y_0$, wherein $y_0$ designates a constant.

If stretching or compression and the shift are e.g. controlled by an affine function of the form $\Delta y(y)=\alpha y+y_0$, then all fields in the distance and near portions as well as in the progression zone are equally affected by the change. However, it is often preferred to obtain specific properties of the distance or the near portion and to only vary the position of the progression zone. Preferably, a function $\Delta y(y)$ having specific characteristics is selected then, e.g. which is steeper in the progression zone than in the distance or the near portion, generally a function of the form $\Delta y(y)=f(y)+y_0$. A positive value of the derivative f'(y) represents a local stretching, a negative value represents a local compression.

Preferably, f(y) is monotonic and also preferably, |f'(y)| is higher in the progression zone than in the distance or the near portion, so that these are affected more strongly by stretching or compression. Preferably, the transform Y depends on the difference of the vertical position of the distance and/or the near reference point of the individual spectacle lens design and the difference of the vertical position of the distance and/or the near reference point of the starting design.

For the function $f(y)$, there are different possibilities of parametrization.

Examples of suitable functions are:

a) $f(y)=\alpha_y$, wherein $\alpha$ designates a constant;
b) double-asymptote with transform coefficients a, b, c, m, d:

$$f(y) = b + \frac{a}{(1+e^{c(y+d)})^m}$$

c) Sigmoid $$f(y) = \frac{a}{1+e^{c(y+d)}}$$

(special case of double-asymptote)
d) Gaussian cumulative function with transform coefficients a, b, c:

$$f(y) = \frac{a}{2}\left(1 + \mathrm{erf}\left(\frac{y-b}{\sqrt{2}\,c}\right)\right)$$

d) Lorentz cumulative function with transform coefficients a, b, c $$f(y) = \frac{a}{\pi}\left(\arctan\frac{y-b}{c}\right) + \frac{\pi}{2}$$

f) Cumulative SDS function with transform coefficients a, b, c, d:

$$f(y) = \frac{a}{2c}\left(2d\ln\left(\exp\left(\frac{2y+c}{2d}\right) + \exp\left(\frac{b}{d}\right)\right) - 2d\ln\left(\exp\left(\frac{y}{d}\right) + \exp\left(\frac{2b+c}{2d}\right)\right) + c\right)$$

g) Logistic dose-response function with transform coefficients a, b, c $$f(y) = a\bigg/\left(1 + \left(\frac{y}{b}\right)^c\right)$$

h) Log-normal cumulative function with transform coefficients a, b, c:

$$f(y) = \frac{a}{2}\mathrm{erfc}\left(-\ln\left(\frac{y}{b}\right)\bigg/\sqrt{2}\,c\right).$$

Further preferably, determining or calculating an individual spectacle lens design, and in particular calculating the location and/or the size of a distance, a near and a progression zone of the spectacle lens design, is performed taking into account one or more of the collected individual data of the spectacle wearer. The individual data of the spectacle wearer, which is taken into account in the calculation of the individual spectacle lens design, particularly comprises one or more of the above-mentioned data or sets of data (e.g. refraction data or power parameters; pupillary distance, the corneal vertex distance (CVD), forward inclination (FI), face form angle (FFA), frame data, centration data (such as tilting of the spectacle lens in front of the eye and corrected PD for fitting, i.e. CorPD), etc.).

Furthermore, according to the invention, a computer program product and a storage medium with a computer program stored thereon are provided, wherein the computer program is adapted, when loaded and executed on a computer, to perform the inventive method for determining or calculating an individual spectacle lens design for a progressive spectacle lens.

Furthermore, according to the invention, an apparatus for determining or calculating an individual spectacle lens design for a progressive spectacle lens for correction of a visual defect of a specific spectacle wearer is proposed, comprising;
  obtaining means for obtaining individual data of the spectacle wearer;
  calculating or optimizing means for calculating the individual spatial position of a distance and/or a near reference point depending on the individual data of the spectacle wearer, according to the inventive method for calculating the individual spatial position of a distance and/or a near reference point;
  calculating or optimizing means for calculating the spatial position and/or the size of a distance, a near and a progression zone of the spectacle lens design depending on the calculated individual spatial position of the distance and/or the near reference point.

Furthermore, according to the invention, a graphical user interface for specifying or determining and presenting, or displaying, an individual spectacle lens design for a progressive spectacle lens is proposed, comprising:
  at least one individual data input portion adapted to input individual data of the spectacle wearer; and
  at least one display portion adapted to present the individual spectacle lens design, wherein the individual spectacle lens design is calculated and determined according to a preferred method for calculating the individual spectacle lens design.

Also, a method is provided according to which an adaptation of the prescription values and the values of wear is performed on the basis of data relating to the object distances distance and near in the refraction determination and data relating to individual object distances.

distance: $\mathrm{sphF}_K = sphF_R + OF_R - OF_G$ near: $\mathrm{sphN}_K = sphN_R + ON_R - ON_G$ $\mathrm{add}_K = sphN_K - sphF_K$, wherein:
$\mathrm{sphF}_R$, $\mathrm{sphN}_R$: spherical values in distance and near of the refraction determination;
$\mathrm{sphF}_K$, $\mathrm{sphN}_K$: corrected spherical values in distance and near;
$\mathrm{add}_K$ corrected addition;
$OF_R$, $ON_R$: reciprocal values of the object distances (signed) in distance and near of the refraction determination;
$OF_G$, $ON_G$: reciprocal values of the object distances (signed) in distance and near in the actual situation of wear.

The individual object distances in particular comprise working distance when reading (near work), working distance in the distance; and/or data relating to the object distances in the refraction determination: distance and near.

The information on the object distances distance and near are taken into account in the calculation or optimization. Thus, the ray path corresponding to the actual situation of wear can be simulated in a better way and the imaging quality can thus be improved.

A method for producing an individual progressive spectacle lens with a variably adjustable, vertical position of the distance and/or the near reference point comprises the following steps:

obtaining individual data of the spectacle wearer;
determining or calculating in the individual vertical and/or the horizontal position of the distance and/or the near reference point depending on the collected individual data of the spectacle wearer;
calculating an individual spectacle lens design, wherein the calculation of an individual spectacle lens design comprises calculating the spatial position and/or the size of a distance, a near and/or a progression zone of the spectacle lens design depending on the determined individual, spatial position of the distance and/or the near reference point;
calculating or optimizing the spectacle lens according to the individual spectacle lens design.

Preferably, calculating or optimizing the spectacle lens is performed taking at least parts of, preferably however all, collected individual data of the spectacle wearer into account.

As explained above, calculating the individual spectacle lens design comprises creating and calculating the target values for the spatial distribution of at least one aberration of the spectacle lens (in particular target values for the spatial distribution of the astigmatic deviation and/or the refraction error), wherein the aberrations assigned to the design are as small as possible, preferably substantially zero, in the individually determined distance and/or near reference point(s).

The calculation or optimization of the spectacle lens according to the individual spectacle lens design preferably is carried out by minimizing a target function in which the individually determined target values associated to the design for at least one aberration are taken into account.

Preferably, calculation or optimization of the spectacle lens is carried out by minimizing a target function of the form:

$$F(\vec{x}) = \sum_{i=1}^{m} [g_{i,S}(S_i - S_{i,target})^2 + \ldots]$$

where:
$S_{i,target}$ is the local target value for the spatial distribution of at least one optical property at the $i^{th}$ evaluation point;
$S_i$ is the actual local optical property at the $i^{th}$ evaluation point;
$g_{i,S}$ the local weighing.

Preferably, the optimization of the progressive spectacle lens is carried out by minimizing an objective function of the form:

$$F(\vec{x}) = \sum_{i=1}^{m} [g_{i,\Delta R}(\Delta R_i - \Delta R_{i,target})^2 + g_{i,Ast}(Ast_i - Ast_{i,target})^2 + \ldots]$$

In the above formula
$\Delta R_{i,target}$ is the target value of the local refractive error at the $i^{th}$ evaluation point;
$\Delta R_i$ is the actual local refractive error at the $i^{th}$ evaluation point;
$Ast_{i,target}$ is the target value of the local astigmatic deviation or the local astigmatic error at the $i^{th}$ evaluation point;
$Ast_i$ is the actual local astigmatic deviation at the $i^{th}$ evaluation point;
$g_{i,\Delta R}$ is the local weighing of the refractive error at the $i^{th}$ evaluation point;
$g_{i,Ast}$ is the local weighing of the astigmatic deviation at the $i^{th}$ evaluation point.

Preferably, the calculation or optimization of the spectacle lens is performed taking into account individual data of the spectacle wearer. Particularly preferably, the calculation or optimization of the spectacle lens is performed online.

Furthermore, the production method comprises:
providing surface data of the calculated and optimized spectacle lens; and
fabricating the spectacle lens according to the provided surface data of the spectacle lens.

Fabrication and machining may be carried out by means of CNC machines, by means of casting methods, a combination of the two methods or by means of another suitable method.

Furthermore, according to the invention, an apparatus for producing an individual progressive spectacle lens having a variably adjustable, individual vertical position of the distance and/or the near reference point is provided, comprising:
design calculating means adapted to perform a preferred inventive method for calculating an individual spectacle lens design;
optimizing or calculating means adapted to perform a calculation and an optimization of the spectacle lens according to the individual spectacle lens design.

In particular, the design calculating means comprise:
obtaining means for obtaining individual data of the spectacle wearer;
calculating or optimizing means for calculating the individual spatial position of a distance and/or a near reference point depending on the individual data of the spectacle wearer, according to the inventive method for calculating the individual spatial position of a distance and/or a near reference point;
calculating or optimizing means for calculating the spatial position and/or the size of a distance, a near and/or a progression zone of the spectacle lens depending on the calculated individual spatial position of the distance and/or the near reference point.

Furthermore, the apparatus for producing an individual spectacle lens with a variably adjustable vertical position of the distance and/or the near reference point preferably comprises machining means for finishing the spectacle lens. The machining means may comprise e.g. CNC machines for direct machining of a blank according to the individual optimization values. Preferably, the finished spectacle lens has a simple spherical or rotationally symmetric aspherical surface and an aspherical/atoric, progressive free-form surface optimized individually according to the individual design values calculated according to the invention and individual parameters of the spectacle wearer. Preferably, the spherical or rotationally symmetric aspherical surface is the front surface (i.e. the object-side surface) of the spectacle lens. Of course, it is also possible to arrange the individually optimized surface on the front surface of the spectacle lens. It is also possible for both surfaces of the spectacle lens to be individually optimized, progressive surfaces.

Preferably, the apparatus for producing an individual progressive spectacle lens further comprises obtaining means for obtaining individual data of the spectacle wearer, which in particular comprises data relating to the individual dioptric power of the spectacle lens required for the spectacle wearer.

The inventive methods and apparatuses for determining the individual position of the distance and/or the near reference point and for determining or calculating an individual spectacle lens design with variably adjustable positions of the distance and/or the near reference point are particularly characterized in that in addition to an automatic adaptation to the individual power parameters, an individual adaptation of the position or location(s) of the distance and/or the near reference point and a therewith-related adaptation of the location and size of the viewing zones is possible. In addition, it is also possible to perform an automatic adaptation of the design to the individual spectacle lens frame taking into account the frame shape and the individual parameters (pupillary distance, corneal vertex distance, forward inclination, face form angle, etc.). Thereby, an optimum physiological infraduction is ensured at any time. Moreover, it is possible to take the individual near distance into account and to freely select the base curve, which is particularly advantageous in the case of modern, more strongly bent frames. Also, an individual pre-decentration may be taken into account. By optimally matching the spectacle lens design or the spectacle lens to the needs and individual data of the spectacle wearer, the compromises of a standard progressive lens are reduced considerably.

The inventive methods and apparatuses for determining the individual position of the distance and/or the near reference point and for determining or calculating an individual spectacle lens design with variably adjustable positions of the distance and/or the near reference point thus allow the creation of individual spectacle lens designs and the production of individual spectacle lenses with largest possible viewing zones according to vision needs. For the spectacle wearer, this results in considerable advantages, such as a relief of eyes and cervical spine, and a reduction of viewing stress and eye fatigue, as well as an optimum vision and wearing comfort.

Preferred embodiments of the invention will be exemplarily described with reference to the figures.

BRIEF DESCRIPTION OF THE FIGURES

The figures show:

FIG. 2 an example of a mask or graphical user interface for inputting individual customer parameters;

FIG. 5 an example of a mask or graphical user interface for inputting individual customer parameters;

FIG. 13 an example or an order form;

FIGS. 16a,b two examples of non-permanent stampings of individually calculated progressive spectacle lenses;

FIG. 17 an example of a permanent engraving of a left, individually optimized, progressive spectacle lens;

FIG. 18 an example of a lens packet for an individually optimized spectacle lens;

FIG. 19 a key to the pictograms used on the lens packet;

DETAILED DESCRIPTION OF THE PREFERRED EMBODIMENTS

Figure 1:
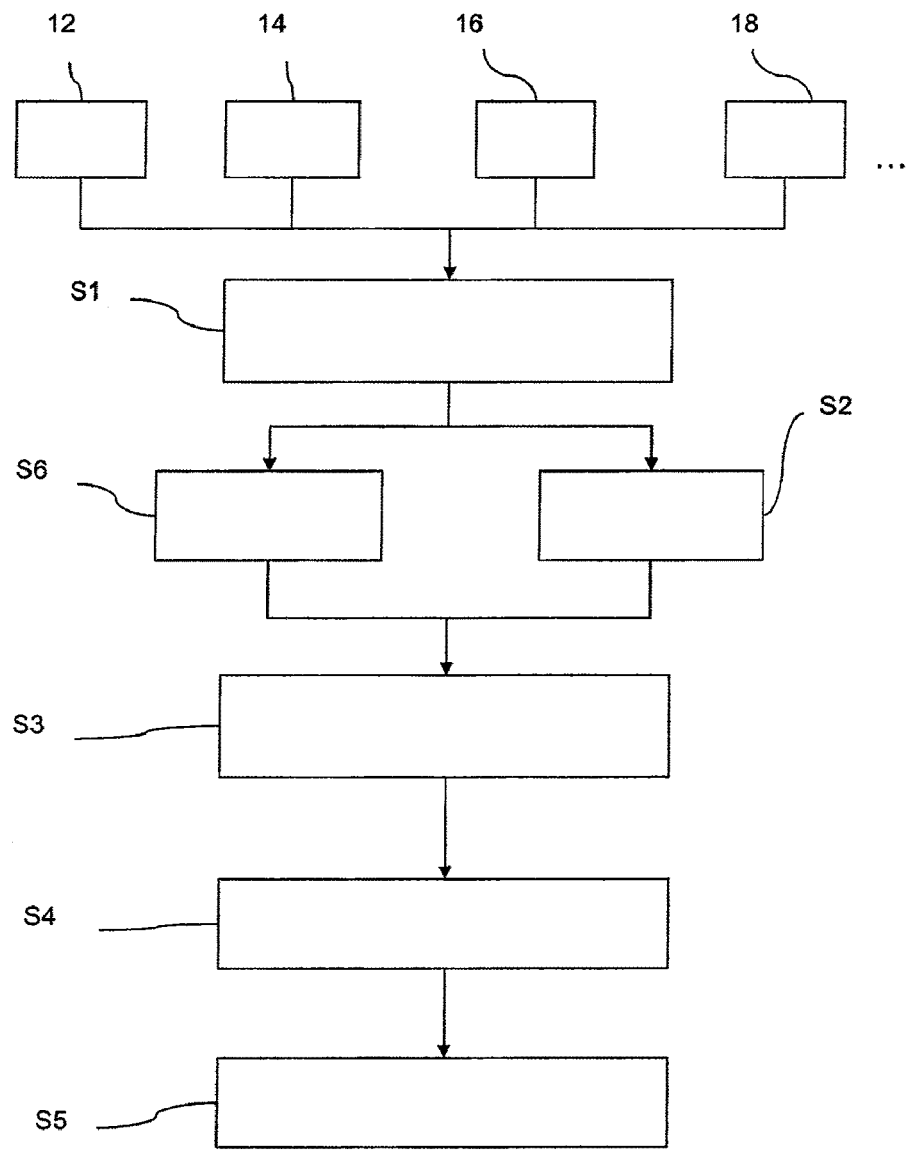
FIG. 1 a schematic flowchart of a method for determining the individual positions of the distance and near points and for determining an individual spectacle lens design.

FIG. 1 shows a schematic flowchart of an exemplary method for determining the individual positions of the distance and near reference points and for determining an individual spectacle lens design with the individual positions of the distance and near reference points.

In a first step (step S1), individual data of the spectacle wearer are collected. The collection of the individual data of the spectacle wearer takes place by means of suitable graphical user interfaces (GUI) which allow for the input and optionally the change of the input individual data of the spectacle wearer.

The optimum spatial position of the distance and/or the near reference point for a specific spectacle wearer in a specific situation of wear is calculated on the basis of the collected individual data (step S2).

In a further step (step S3), a progressive lens design or a proposal for a progressive lens design is calculated with the optimum positions of the distance and near reference points determined in the second step S2. This design proposal is visualized by means of suitable graphical user interfaces, wherein the user has the possibility to actively vary the design by changing the individual position of the distance and/or the near reference point and/or changing the individual customer data (in particular the preferences relating to the viewing zones, the frame data, etc.).

Preferably, the spectacle lens design is derived from an existing spectacle lens design with a fixed spatial positions of the distance and near reference points on the basis of the freely determinable, individual positions of the distance and/or the near reference point determined from the individual customer data, wherein the design characteristic is maintained. Subsequently, the vertical position and length of the progression zone of the progressive surface is automatically matched to the individual situation of wear.

The collected individual data of the spectacle wearer preferably comprises individual refraction data 12 (sphere, cylinder, axis position, addition, prism and base); individual frame and centration data 14 (vertical lens size and centration height, frame shape, distance between the lenses AZG); individualization parameters or individual parameters 16 of the eyes of the spectacle wearer and/or the individual situation of wear or position of wear of the spectacles in front of the eyes of the spectacle wearer (in particular pupillary distance PD), corneal vertex distance CVD, forward inclination FI, face form angle FFA, etc.); data 18 relating to the individual preferences and weightings of the viewing zones as well as further individual data.

The individual parameters of the eyes of the spectacle wearer and/or the individual situation of wear or position of wear (pupillary distance, corneal vertex distance, forward inclination, face form angle, etc.) may be determined automatically by means of a suitable 3D measuring apparatus, such as the 3D video centering apparatus ImpressionIST of the company Rodenstock GmbH. Alternatively, the individual parameters may be determined by means of conventional measuring tools.

The individual parameters may for example vary in the following ranges:
pupillary distance (PD) from 30 to 80 mm
corneal vertex distance (CVD) from 3 to 50 mm
forward inclination (FI) from −10 to +20 degrees
face form angle (FFA) from −10 to +35 degrees.

The frame and centration data may be input by the user (e.g. an optician or an optometrist), be automatically determined by means of a tracer or be retrieved e.g. from a database. Also, the centration data may be applied directly from a 3D video centering system (e.g. 3D video centering system ImpressionIST of the company Rodenstock GmbH).

The collected individual data of the spectacle wearer is taken into account in the calculation and the optimization of the spatial position, in particular the vertical and/or the horizontal position of the distance and/or the near reference point, as will be explained in detail in the following. Moreover, the collected individual data of the spectacle wearer are taken into account in the calculation or optimization of the spectacle lens.

In a fourth step (step S4), an individual spectacle lens is optimized and calculated, wherein the optimization is performed taking into account at least part of the collected individual data, in particular data relating to the individual parameters of the spectacle wearer and the individual position of wear (face form angle, forward inclination, pupillary distance, corneal vertex distance, etc.).

The fabrication of the individually calculated spectacle lens is e.g. performed by means of precision machines, preferably CNC grinding and polishing machines (step S5).

FIG. 2 shows a graphical user interface for inputting individual customer parameters.

FIG. 2 shows an example of a graphical user interface 20 for inputting individual data (prescription values) of the spectacle wearer. The individual data may be directly input into the corresponding input fields or sections of the mask or graphical user interface, or be e.g. retrieved from a database. The fields with a gray background are automatically calculated and filled with data by the program.

The graphical user interface 20 shown in FIG. 2 includes:
a section "prescription values" (section 22) comprising input fields for inputting individual refraction data, such as sphere "sph", cylinder "cyl", axis, prism, base;
a section "individual parameters" (section 24) comprising input fields for inputting individual parameters of the eyes of the spectacle wearer and/or the individual position of wear (pupillary distance "PD", corneal vertex distance "CVD", forward inclination "FI", face form angle "FFA");
a section "frame and centration data" (section 26) comprising input fields for inputting frame and centration data (fitting height, horizontal lens size, vertical lens size, distance between lenses "AzG" or "AZG") and optionally a display section (section 27) for displaying the centration of the spectacles matched to the box dimension.

The frame data can be input into corresponding input fields. These values may be entered automatically if the frame is e.g. selected by means of a tracer or from a list of frames. With a function "match to box dimension", the frame can be matched to the possibly changed frame data.

In the section "frame and centration data", a frame can be selected from a database e.g. if no frame has been applied or measured by means of a tracer before. In particular, the frame can be selected from a list in an opening pop-up window. The shape and frame data are preferably displayed as well. The selection can be applied by confirming it. Also, an approximate frame can be selected from a number of different frame shapes ("approximate shapes"). Here, another pop-up window may open in which the frame can be selected from a choice of common shapes.

The graphical user interface 20 shown in FIG. 2 further includes:
sections or input fields for inputting further information, such as coating (cf. section 28 in FIG. 2), color (cf. section 30 in FIG. 2); as well as
a section or input field "base curve" (section 34) into which the base curve fitting the selected frame best can be entered.

As explained above, the optimum spatial position of the distance and/or the near reference point for a specific spectacle wearer in a specific situation of wear is calculated on the basis of the collected individual data (step S2 in FIG. 1). The calculation of the optimum spatial position of the reference points or design points according to the inventive methods and by means of the inventive computer program will be described in detail in the following by means of examples.

The vertical height of the distance reference point may preferably be determined flexibly, depending on the individual data of the spectacle wearer, in a range between +4 to −4 mm with respect to the centration or fitting point set for this spectacle lens by the manufacturer. The near reference point may preferably be determined flexibly between 13 and 20 mm vertically below the centration or fitting point. This results in a flexibly selectable progression length, which may preferably have a minimum of 13 mm and a maximum of 24 mm. Preferably, the distance and near reference points can be freely determined in steps of 0.1 mm within an admissible range.

Preferably, on the basis of the frame and centration data, a limit calculation for the location of the distance and near reference points is performed. Thereby, it is ensured that the distance and near reference points lie within the frame. Preferably, the minimum vertical distance from the lower frame edge to the near reference point is 2 mm. The distance reference point preferably has a minimum vertical distance of 6 mm, preferably of 8 mm, from the upper frame edge. The maximally admissible progression length can be calculated with the help of the minimally admissible distances of the distance and near reference points from the upper and lower frame edge, respectively. The progression length is defined as the vertical distance between the distance referent point and the near reference point.

Furthermore, on the basis of the frame and centration data, an ideal location of the positions of the distance and near reference points is calculated with respect to the frame and centration data. Preferably, the ideal vertical distance from the lower frame edge to the near reference point is at least 5 mm. The ideal vertical distance of the distance reference point from the upper frame edge is preferably at least 12 mm. If deviating reference point locations arise due to different centration heights in the frame to the right/left, these are preferably brought in balance. In this way, it is ensured that the reference points are always within the frame and at the same height.

The minimum progression zone length can be calculated from the ideal distances of the distance and near reference points from the respective frame edge. The user (e.g. optician/optometrist) can directly communicate these values together with the order or calculate them with the inventive computer program.

The individual parameters (pupillary distance PD, corneal vertex distance CVD, forward inclination FI, face form angle FFA, etc.), which are for example automatically determined by means of a suitable 3D measuring apparatus, such as by means of the 3D videocentering apparatus ImpressionIST by the company Rodenstock GmbH, or alternatively by means of conventional measuring tools, are taken into account in the calculation or optimization of the spatial positions, in particular the vertical and/or the horizontal position of the distance and/or the near reference point, as will be explained in detail in the following.

The individual parameters may for example vary in the following ranges:
pupillary distance (PD) from 30 to 80 mm
corneal vertex distance (CVD) from 3 to 50 mm
forward inclination (FI) from −10 to +20 degrees
face form angle (FFA) from −10 to +35 degrees.

The spatial position, in particular the vertical distance(s), of the distance and/or the near reference point from the centration point, depends particularly on the forward inclination and the corneal vertex distance. The standard value or the value underlying a standard or basic design is e.g. 9 degrees for the forward inclination and 13 mm for the corneal vertex distance. If the actual values (CVD and forward inclination) deviate therefrom, the vertical position of the reference points is adapted accordingly according to the invention, in order to avoid e.g. extremely high sight deviations in near vision with low CVD values.

This may be done e.g. by means of the following formula:

$$y_{Bnew} = y_{Bold} * (CVD + 13.5 \text{ mm})/26.5 \text{ mm} * \cosine(\text{forward inclination})/\cosine(9 \text{ degrees}),$$

wherein:
$y_{Bnew}$ designates the new vertical position of the distance and/or the near reference point;
$y_{Bold}$ designates the vertical position of the distance and/or the near reference point according to the standard design.

If the thus calculated values are outside the admissible interval calculated from the frame and centration data, the position of the reference points is changed until the reference points lie within the admissible interval. Preferably, the vertical heights of the distance and/or the near reference point at the left/right (i.e. for the left and the right eye)—as described above—are matched to each other.

The individual data of the spectacle wearer may further comprise data relating to the previous lenses, in particular
data relating to the type of the spectacle lens (single-vision, bifocal, progressive), and/or the progression length;
data relating to the dioptric power, in particular the addition of the previous lens.

Furthermore, data relating to the material (plastic/silicate) and/or the refractive index of the previous lens may be determined and evaluated. If a progressive lens has been worn before, the data relating to the previous lens may further comprise data relating to the design of the spectacle lens (hard/soft) and/or the type of the progressive lens (individual, conventional).

The data relating to the type of the spectacle lens (single-vision, bifocal, progressive) and the progression length of the previous lens may be taken into account in the optimization of the spatial positions of the distance and near reference points, the optical power, etc., Furthermore, the data relating to the previous lens may comprise data relating to desired improvements with respect to the previous lens, for example larger distance zone, larger intermediate zone, larger near zone, less infraduction when reading, or less rocking motion.

From the location of the reference points of the previous progressive lens and possibly existing improvement wishes, for example an ideal individual location of the reference points with respect to the previous history may be calculated. For example, if the distance zone has been too small so far and/or if an improved distance vision is required, the distance reference point is shifted downward with respect to the previous location. If the near zone has been too small and/or if the infraduction when reading was too large, the near reference point is shifted upward. If the intermediate zone for working e.g. at a computer has been too small and/or if the rocking motion has been too great, the distance reference point is shifted upward and the near reference point is shifted downward.

The individual data of the spectacle wearer may further comprise data relating to the preferences with respect to the viewing zones (distance, near and intermediate or progression zone). The query of these data may for example take place by means of suitable graphical user interfaces. Preferably, the data are also taken into account in the calculation of the optimum location of the distance and/or the near reference point.

In particular, an ideal location of the reference point may be calculated with respect to the preferences. For example, if the spectacle lens is mainly used when driving a car, the distance reference point is shifted downward with respect to the physiologically ideal value. For example, if the spectacle lens is mainly used for reading, the near reference point is shifted upward with respect to the physiologically ideal value. For example, if the spectacle lens is mainly used for computer work, the distance reference point is shifted upward and the near reference point is shifted downward with respect to the physiologically ideal values.

Likewise, from the so-far worn spectacle lens and the desired improvements, an ideal location of the reference points (distance and near reference points) may be determined with respect to the desired improvements.

For example, if the distance zone has been too small so far and/or if an improved distance vision is desired, the distance reference point is shifted downward with respect to the previous location. If the near zone has been too small and/or the infraduction when reading has been too great, the near reference point is shifted upward. If the intermediate zone for working e.g. at a computer has been too small and/or if the rocking motion has been too great, the distance reference point is shifted upward and the near reference point is shifted downward.

For the lens order, the optician/optometrist can specify an ideal individual position of the distance and/or the near reference point on the basis of the determined preferences with respect to the viewing zones and optionally to the desired improvements themselves. Preferably, however, the ideal position is calculated from the determined preferences and optionally desired improvements automatically with the aid of a computer. For example, this may take place as follows:

On the basis of the determined individual preferences, weighting (PreferenceDistance, PreferenceNear, PreferenceIntermediateZone) may be associated to the individual viewing zones. The individual weightings may for example assume values from 0 to 100, wherein the sum of the individual weightings is between 0 and 100.

The ideal vertical location of the distance and near reference points with respect to the viewing zone preferences may for example be calculated as follows:

If the weighting of the distance zone (PreferenceDistance) is smaller than 33, it follows that:

$Y_{BF}=4-4*PreferenceDistance/33.33$ otherwise $Y_{BF}=0-4*(PreferenceDistance-33.33)/66.66.$ if the weighting of the near zone (PreferenceNear) is smaller than 33, if follows that:

$Y_{BN}=-20+2*PreferenceNear/33.33$ otherwise $Y_{BN}=-18+5*(PreferenceNear-33.33)/66.66.$ If the weighting of the intermediate zone (PreferenceIntermediateZone) is smaller than 33, it follows that:

progression length=13+5*PreferenceIntermediateZone/33.33 otherwise progression length=18+2*(PreferenceIntermediateZone-33.33)/66.66.

Since the reference points and the progression zone are not independent of each other, but the progression length represents the difference of the vertical location of the reference points, the vertical positions of the reference points may preferably also be calculated from the progression length:

$Y_{BF2}=Y_{BN}+progression\ length$ $Y_{Bn2}=Y_{BF}-progression\ length$

The final reference points then result in:

$Y_{BF}=(GW1*Y_{BF}+Y_{BF2})/(g_1)$ $Y_{BN}=(GW2*Y_{BN}+Y_{BN2})/(g_2)$ $g_1=GW1+1$
$g_2=GW2+1$

The weightings GW1 and GW2 preferably assume values between 1 and 2.

Likewise, from the data relating to the so-far worn spectacle lens and data relating to the desired improvements, an ideal location of the reference points (distance and near reference points) with respect to the desired improvements may be determined by means of suitable allocation of weightings.

Furthermore, the individual data of the spectacle wearer may comprise data relating to the main use (driving a car, computer work, reading, crafts, etc.) of the progressive lens.

Likewise, an ideal location of the reference points may be calculated from the data relating to the main use. For example, if the spectacle lens is mainly used when driving a car, the distance reference point is shifted downward with respect to the physiologically ideal value. For example, if the spectacle lens is mainly used for reading, the near reference point is shifted upward with respect to the physiologically ideal value. For example, if the spectacle lens is mainly used for computer work, the distance reference point is shifted upward and the near reference point is shifted downward with respect to the physiologically ideal values.

Moreover, the individual data of the spectacle wearer may comprise data relating to:
- environmental influences (brightness of the surrounding, etc.); and/or
- individual main direction of sight distance and near, and/or potentially present, unusual head and body postures;
- physiological parameters of the eyes of the spectacle wearer, in particular visus with correction, threshold of stereopsis.

Accordingly, suitable graphical user interfaces for inputting and optionally correcting data may be provided.

In addition, data relating to the preference aesthetics/optics may be collected, and the material of the spectacle lens may be determined on the basis of this data. In the case of a higher weighting of the preference aesthetics, a highly refractive material is selected, which is very thin and light. In the case of a higher weighting of the optics, a material with a higher Abbe number is selected, which exhibits very good optical properties. This selection may also depend on power.

Individual data of the spectacle wearer is collected and evaluated and controls the location of the reference points "distance" and "near".

For example, an ideal location of the reference points may be obtained and calculated with respect to the frame and centration data, the physiology and ergonomics, the previous history, the preferences, and optionally other relevant individual data of the spectacle wearer. In other words, an ideal location of the reference points (distance and near reference points) may be determined with respect to different categories (frame and centration data, physiology and ergonomics, previous history, preferences, etc.).

From these data, an optimum compromise may be made e.g. by averaging. The different categories may be weighted differently. The calculation of the optimum location of the distance and/or the near reference point $y_{DF,DN}$ may for example be calculated by means of the following formula:

$$y_{DF,DN} = \sum_{i=1}^{N} g_i y_{DF,DN}^i$$

$$\sum_{i=1}^{N} g_i = 1$$

wherein:
$g_i$ designates the weighting of the $i^{th}$ category;
$y_{DF,DN}^i$ designates the ideal position of the distance reference point (design point distance) DF and the near reference point (design point near) DN, respectively, for the $i^{th}$ category; and
N designates the number of different categories.

Furthermore, the individual data of the spectacle wearer may comprise data relating to the optical parameters. On the basis of the determined optical parameters, preferably a conversion of the addition, the near distance and the addition or additional parameters may take place (step S6 in FIG. 1). The data relating to the optical parameters comprise in particular data relating to the individual optic distances, such as working distance when reading (near work), working distance in the distance and/or data relating to the object distances distance and near in the refraction determination.

The data on the object distances "distance" and "near" in the refraction determination are taken into account in the calculation or optimization. Thus, the ray path corresponding to the actual situation of wear can be simulated more precisely and the imaging quality can consequently be improved.

If the object distances "distance" and "near" of the refraction determination are known, an adaptation of the prescription values or the values of wear may preferably be performed. This may for example take place by means of the following calculation:

distance: $sphF_k = sphF_R + OF_R - OF_G$ near: $sphN_k = sphN_R + ON_R - ON_G$ $add_K = sphN_K - sphF_K$, wherein:

$sphF_R$, $sphN_R$: spherical values in distance and near of the refraction determination;

$sphF_K$, $sphN_K$: corrected spherical values in distance and near;

$add_K$ corrected addition;

$OF_R$, $ON_R$: reciprocal values of the object distances (signed) in distance and near of the refraction determination;

$OF_G$, $ON_G$: reciprocal values of the object distances (signed) in distance and near in the actual situation of wear.

In particular, it is possible to take the main visual distance in near vision in the actual position of wear of the spectacle lens into account when calculating the lens.

If the optimum individual position of the distance and/or the near reference point is determined on the basis of individual data of the spectacle wearer, a corresponding spectacle lens design is automatically calculated with the thus determined positions of the distance and near reference points and optionally taking into account the individual parameters of the spectacle wearer (step S3 in FIG. 1).

Figure 3:
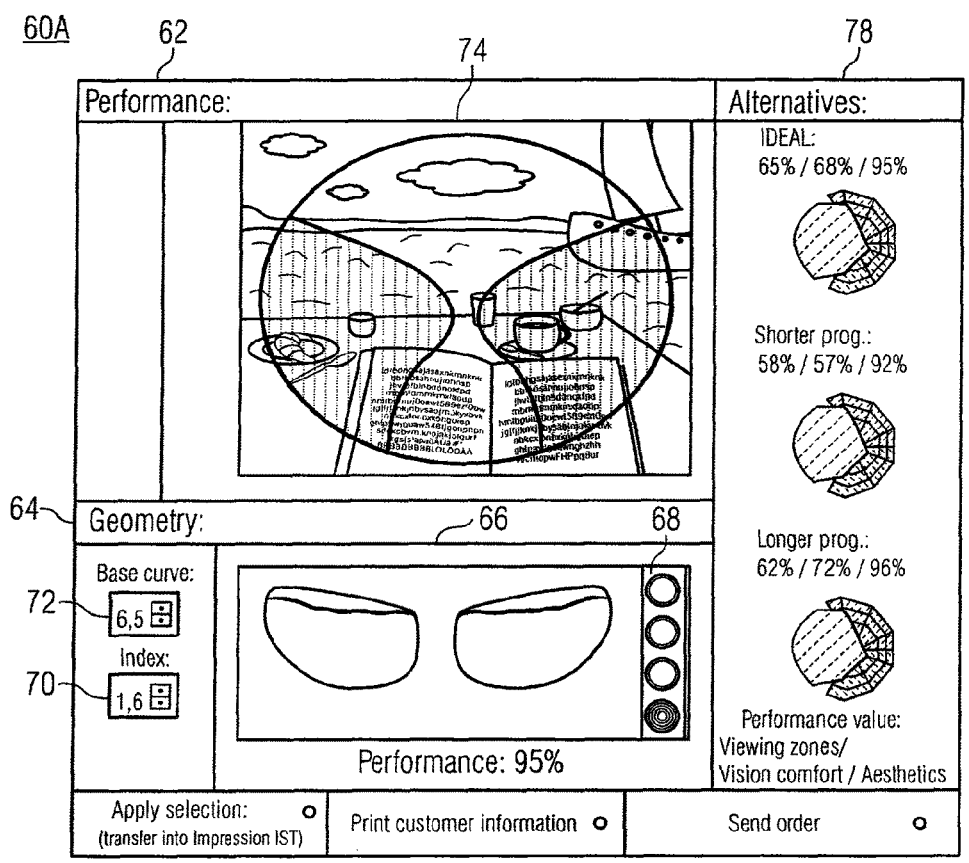
FIG. 3 an example of a graphical user interface for result presentation.

The design proposal may be visualized for the sake of result presentation by means of a suitable graphical user interface 60A (cf. FIG. 3). Depending on the selection in the settings, a graphical user interface 60B (design tuner) may be shown in addition (cf. FIG. 4) with which, in addition to a result presentation, the user is given the possibility to actively change the design by changing the individual position of the distance and/or the near reference point and/or by changing the individual data of the spectacle wearer (in particular the preferences, the frame data, etc.). In addition, the corresponding geometric data of the spectacle lens (center thickness, edge thickness, base curve, weight) can be calculated and be visualized as well by means of a suitable graphical user interface (preferably in the form of a three-dimensional module). The graphical user interfaces 60A and 60B are divided into two areas: in the upper area 62, information on the theme "viewing" and/or "performance" with the proposed design for an individual spectacle lens are illustrated; in the lower area 64, information on the theme "appearance" and "geometry" of the individual spectacle lens or spectacles are illustrated.

In the area "appearance" 64, in particular cosmetic properties and data regarding the aesthetics of the spectacle lens (e.g. weight, geometric data, such as fabrication height, maximum edge thickness, center thickness, base curve, etc.) of the edged spectacle lens or edged spectacle lenses can be visualized and illustrated graphically. The visualization of the cosmetic properties of the spectacle lens may e.g. be achieved by means of a three-dimensional graphical presentation of a model of the spectacle lens 66 with the determined geometric data, as is e.g. shown in FIGS. 3 and 4. The presentation of the cosmetic properties of the spectacle lens may be influenced by selection of the base curve and the refractive index. The selection may depend on the power. The area "appearance" 64 may further comprise an area 70 for displaying numerical values relating to the refractive index and an area for displaying the base curve (area 72). The displayed values for the base curve and the refractive index are composed of the power range, the required diameter, the base curve wish and the refraction data. Therefore, deviations from the base curve wish input into the mask "ordered values" are possible. The technically realizable values for the base curve and the refractive index of the lens can be changed via corresponding selection fields. If changes of the default base curve, the refractive index, etc., are made, the graphical illustration and the geometric data can be calculated again according to the changed values by pressing the button "refresh". By means of suitable buttons 68, the use of the edged spectacle lenses may be shown from different static perspectives (frame from above, frame from front, from the side, from obliquely above). For an improved detailed view, the image may be illustrated in an enlarged manner via a corresponding button.

Figure 4:
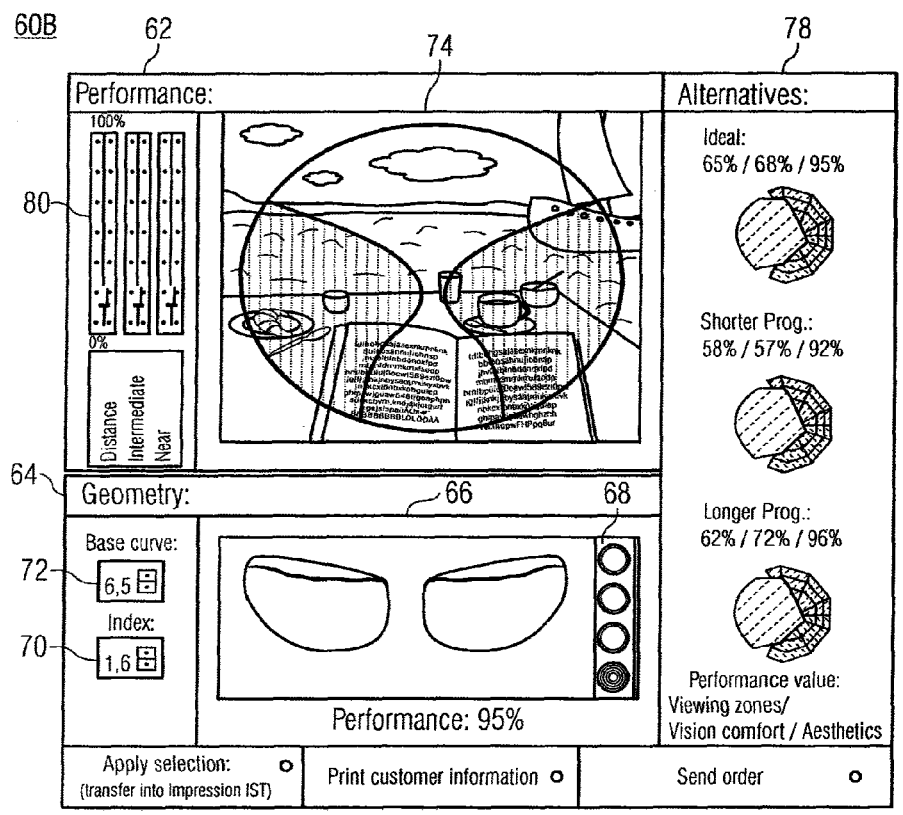
FIG. 4 an example of a graphical user interface for result presentation.

In addition to the visualization of the cosmetic properties of the spectacle lens, a visualization of the optical properties of the spectacle lens takes place (viewing zones, in particular spatial position and size of the individual viewing zones). The presentation of the sizes of the viewing zones may merely take place relative to the prescription data without taking into account a possible material dependence. Of course, consideration of a material dependence may be provided for. FIGS. 3 and 4 show examples of the presentation of the optical properties of the spectacle lens.

Furthermore, a visualisation of the vision comfort (e.g. infraduction, rocking, peripheral vision, distortions, etc.) may be provided for.

In addition, a suitable presentation of performance values relating to the viewing zones, the viewing comfort and/or the cosmetic properties and the aesthetics of the individual spectacle lens may be provided for. Furthermore, performance values of alternative design proposals may be presented as well.

The area "viewing" 62 of the graphical user interfaces 60A to 60D is therefore always divided into several sub-areas. In the sub-area 74 "binocular viewing zone presentation" of the area 62, the design ideal for the customer and specified frame is schematically shown by means of an ellipsis. Gray areas are areas with aberrations (e.g. astigmatism in the position of wear larger than 0.5 D). In the sub-area 78 "design profile" of the area 62, a qualitative comparison of the sizes of the viewing zones with respect to each other is illustrated e.g. in the form of diagrams (cf. FIGS. 3 and 4).

In addition, the optician/optometrist and/or the spectacle wearer may be given the possibility to actively change the thus calculated individual spectacle lens design. For example, the change takes place by actively changing the spatial position, in particular the vertical heights of the distance and/or the near reference point. Alternatively, the weightings of the viewing zones may be changed.

The change or adaptation of the position of the distance and/or the near reference point and/or of the preferences with respect to the viewing zones may for example be performed by means of a suitable graphical user interface. An example of a suitable graphical user interface in the form of a slide control 80, which enables an adaptation of the preferences with respect to the viewing zones, is shown in FIG. 4.

The new spectacle lens with the changed position of the distance and/or the near reference point is preferably calculated and visualized in real time. Preferably, the difference or change of the optical properties of the new spectacle lens design with respect to the old one is visualized as well.

Further embodiments, advantages and characteristics of the invention can be taken from the accompanying exemplary, non-limiting description pages.

In the following, the individually determinable distance and near reference points will be referred to as design point "distance" and design point "near", respectively. In particular, the individually determined distance reference point or design point "distance" corresponds to the point by which the wearer is optimally corrected in their distance vision and which corresponds to the personal viewing habits of the wearer. The individually determined near reference point or design point "near" corresponds to the point by which the wearer is optimally corrected in their near vision and can lower their views as comfortable to them.

Conventional progressive spectacle lenses (multifocal lenses) usually comprise a progressive front surface, while the prescription surface on the eye-side is fabricated after receipt of order. In the fabrication according to the base curve system, a limited number (e.g. 72) of progressive surfaces is used, which are adapted to visual defects, are prefabricated and thus standardized. However, these do not apply separately to each power, but to a certain spectrum of the power range. The optimization of the progressive surfaces only takes place for the mean power per base curve or power range. If the refraction data deviates from the optimized powers, it results in restrictions of the usable viewing zones.

In conventional progressive lenses, already small deviations of the ordered powers in sphere, cylinder, axis or also prism and base from the calculation underlying the blank restrict the possibility that a design lives on, which may cause discomfort with the user. In addition, the optimization of conventional progressive lenses is only based on standard values which often do not satisfy the individuality of the lens, frame and customer data of the wearer.

In the power-optimized progressive lenses, the disadvantages of the conventional progressive lenses are eliminated by an aspherical or atoric prescription surface optimized online for each power combination individually. By means of the Freiformtechnologie (free form technology), it is possible to fabricate power-optimized progressive lenses. Depending on the calculation and fabrication know-how, individual progressive lenses may be fabricated with the Freiformtechnologie as well.

Furthermore, individual progressive lenses are known which can be optimized and calculated taking the individual prescription (sph, cyl, axis, add, prism, base) and the individual positions of the lenses in front of the wearer's eye (CVD, FFA, forward inclination, pupillary distance) into consideration.

A second group of individual progressive lenses is progressive lenses personalized in a different manner, e.g. by personal behaviors of the wearer or their preferences. However, these progressive lenses do not or only partly consider the individual parameters. These progressive lenses are based on a physiognomic standard model usually not corresponding to the actual circumstances and thus leading to optical deviations and/or performance losses.

In all cases however, the design of a progressive spectacle lens has been fixedly defined so far. With a preferred inventive method, it is possible to tailor the spectacle lens design to the customer needs, wherein individual customer parameters (e.g. pupillary distance (PD), corneal vertex distance (CVD), frame shape, forward inclination (FI), face form angle, individual position of the distance and/or a near reference point, individual near distance, etc.) are taken into consideration.

Preferably, the viewing experience and the needs or vision needs of a customer are taken into account in a preferred inventive method for calculating an individual design and for manufacturing a spectacle lens. Thus, it is possible to create an individual progressive spectacle lens using the technical know-how e.g. of an optician with the collaboration of the customer (spectacle wearer). Preferably, advantages and disadvantages of the previous model are taken into consideration.

The individual parameters (e.g. pupillary distance PD, corneal vertex distance CVD, forward inclination FI, face form angle FFA, etc.), which are for example automatically determined by means of a suitable 3D measuring apparatus, such as by means of the 3D video centering apparatus ImpressionIST by the company Rodenstock GmbH, or alternatively by means of conventional measuring tools, are taken into account in the calculation and optimization of the spatial positions, in particular the vertical and/or the horizontal position of the distance and/or the near reference point.

The individual parameters may vary in the following ranges:
pupillary distance (PD): 30 to 80 mm
corneal vertex distance (CVD): 3 to 50 mm
forward inclination (FI): −10 to +20 degrees
face form angle (FFA): −10 to +35 degrees.

Moreover, the special viewing habits of the spectacle wearer may be considered in addition to the individual parameters.

Figure 5:
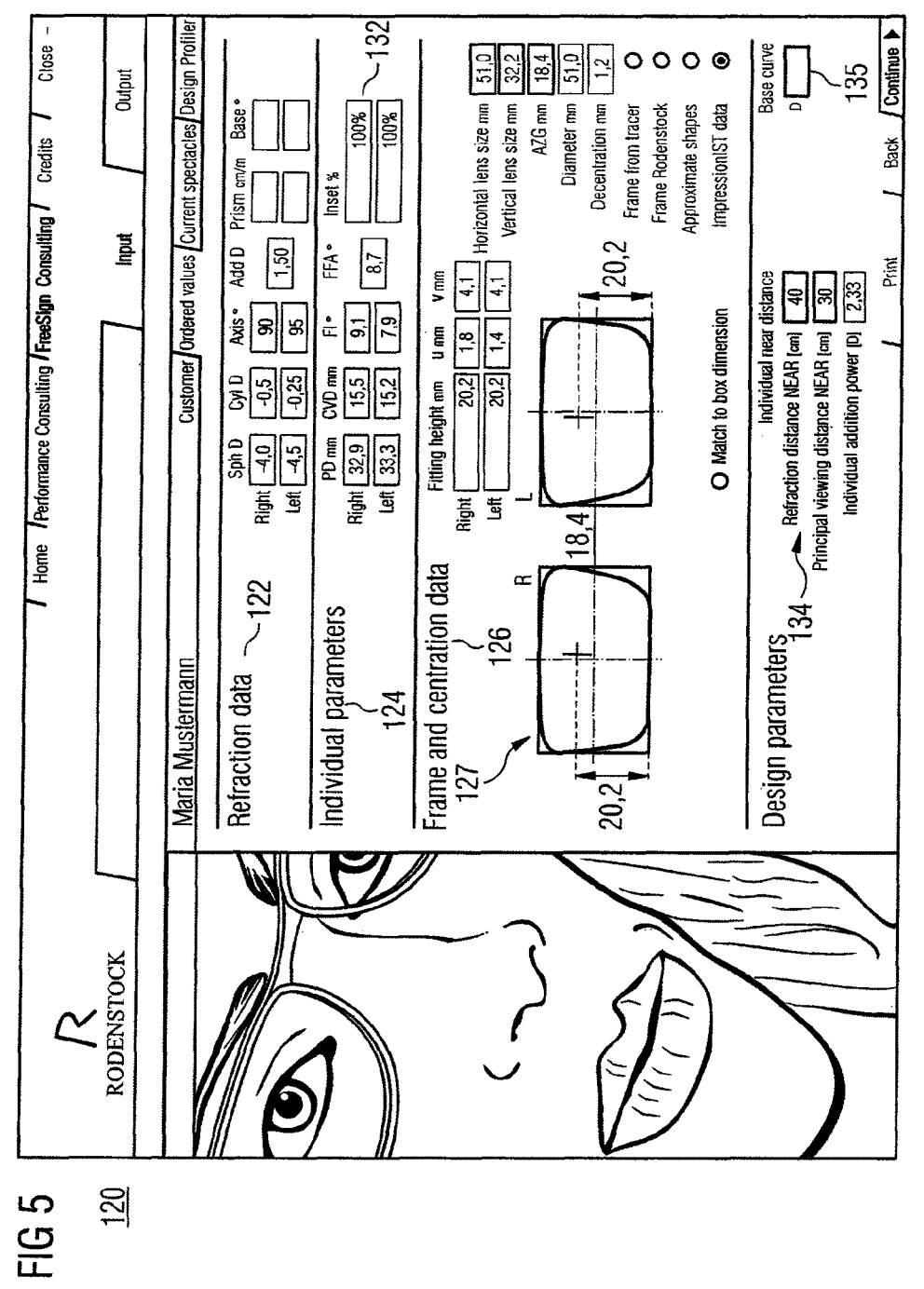
Figure 6:
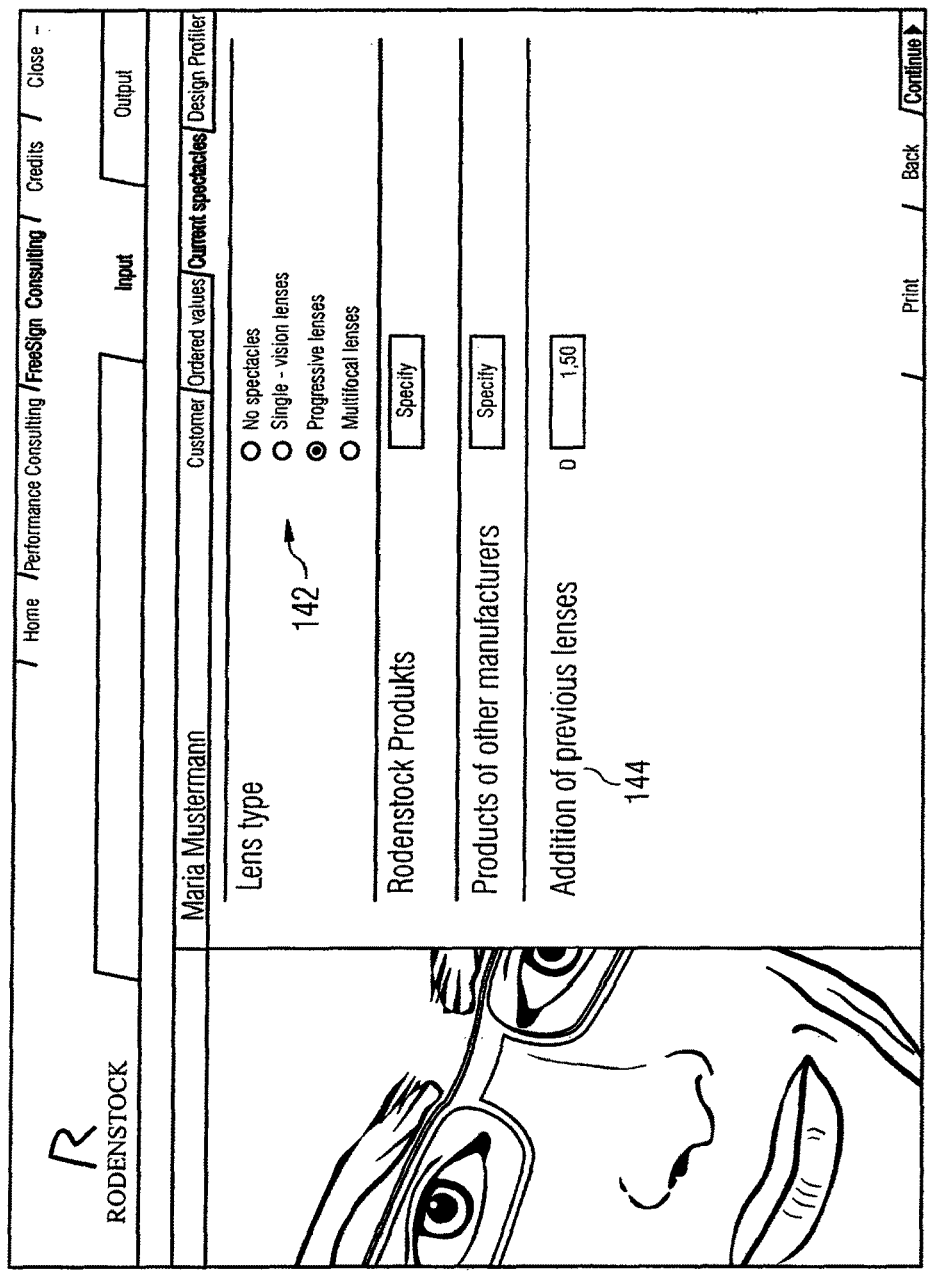
FIG. 6 an example of a mask or graphical user interface for inputting data relating to the current spectacles.
Figure 7:
FIG. 7 an example of a mask or graphical user interface for inputting data relating to the individual preferences and prioritization of the viewing zones.

FIGS. 5 to 7 show graphical user interfaces for inputting individual customer parameters.

For example, in a first mask or graphical user interface (not shown), information on the customer (e.g. name, contact address, frame selection, etc.) can be input or e.g. be imported from a database. The selected frame, which can be directly measured by means of a suitable tracer (e.g. ImpressionIST by the company Rodenstock) or be retrieved from a database, can also be displayed.

FIG. 5 shows an example of a mask or graphical user interface 120 for inputting individual data (prescription values) of the spectacle wearer. The individual data can directly be input into the corresponding input fields or sections of the mask or graphical user interface, or be e.g. retrieved from a database. The fields with a gray background are automatically calculated and filled with data by the program.

The graphical user interface 120 shown in FIG. 5 includes:
a section "refraction data" (section 122) comprising input fields for inputting individual refraction data, such as sphere "sph", cylinder "cyl", axis, prism, base);
a section "individual parameters" (section 124) comprising input fields for inputting individual parameters of the spectacle wearer's eyes and/or the individual position of wear (pupillary distance "PD", corneal vertex distance "CVD", forward inclination "FI", face form angle "FFA");
a section "frame and centration data" (section 126) comprising input fields for inputting frame and centration data (fitting height, horizontal lens size, vertical lens size, distance between lenses "AZG") and optionally a display section (section 127) for displaying the centration of the spectacles matched to the box dimension.

The frame data can be input into corresponding input fields. These values can be entered automatically if the frame is e.g. selected by means of a tracer or from a list of frames. The centration data can optionally directly be applied from a 3D video centering system (e.g. 3D video centering system by the company Rodenstock GmbH). With a function "match to box dimension", the frame can be matched to the possibly changed frame data.

In section 126 "frame and centration data", a frame can be selected from a database e.g. if no frame has been applied or measured by means of a tracer before. In particular, the frame can be selected from a list in an opening pop-up window. The shape and frame data are preferably displayed as well. The selection can be applied by confirming it. Also, an approximate frame can be selected from a number of different frame shapes ("approximate shapes"). Here, another pop-up window may open in which the frame can be selected from a choice of common shapes.

The graphical user interface 120 shown in FIG. 5 further comprises a section or input field "Inset" (section 132). If the spectacle wearer has a convergence behavior in near vision deviating from the standard case, the default value in the input field "Inset" can be changed as appropriate. Preferably, the inset value is calculated considering the individual customer parameters.

Also, the graphical user interface 120 comprises a section 134 "Design Parameter" with corresponding input fields for inputting:
the individual near distance in the refraction determination (refraction distance near);
the principal viewing distance near; and
the individual addition power.

If no data regarding the individual near distance are input, it is assumed that up to an addition of 2.5 D, the individual near distance is 40 cm in the refraction determination. In other words, it is assumed that the ordered addition was determined in 40 cm and that also the principal viewing distance of the spectacle wearer is at this distance. In the case of higher additions, the reciprocal of the addition corresponds to the maximum near distance. If only one of the two input fields "Refraction Distance Near" and "Principal Viewing Distance Near" is filled, it is assumed that the value also holds true for the respective other distance. The inset and the astigmatism are calculated for the principal viewing distance "near".

If different values for the refraction distance "near" and the principal viewing distance "near" are entered into the corresponding input fields, the individual addition power for the principal viewing distance is automatically calculated as well. The individual addition power is displayed if it lies outside the delivery range (0.75 D to 3.50 D) or deviates more than 0.5 D from the ordered addition.
Example:
ordered addition (refraction)=2.00 D, principal viewing distance near=30 cm, refraction distance near=40 cm. The ordered addition of 2.00 D is optimized for 30 cm and the addition is adapted. In addition to the inset, the astigmatism of oblique incidence is corrected for the desired principal viewing distance.

Now, if only one distance (principal viewing distance or refraction distance) is specified, it is assumed that the ordered addition relates to the given distance. Here, no adaptation of the addition takes place and the spectacle lens design or the spectacle lens is calculated and optimized for the ordered addition in the specified near distance. If no near distance (principal viewing direction and/or refraction distance) is specified, it is assumed that refraction has been performed in 40 cm and that this refraction distance corresponds to the principal viewing direction in near vision. Here, no adaptation of the addition takes place and the spectacle lens design or the spectacle lens is calculated and optimized for the ordered addition for 40 cm. Usually, the addition available from the manufacturers lie in a range between 0.75 D and 3.5 D. On the basis of the following simple calculation, the optician can check whether the spectacle lens is available:

$$IZ(dpt) = \text{Add}(dpt) - \left(\frac{1}{RDN(m)}\right) + \left(\frac{1}{MVDN(m)}\right),$$

where:
IZ is the individual addition power in D;
Add is the addition in D;
RDN is the amount of the refraction distance near in meters; and
MVDN is the amount of the principal viewing distance near.

EXAMPLES

Possible:
addition refraction=1.75 D;
refraction distance near=40 cm;
principal viewing distance near=30 cm;
IZ=1.75 D−2.50 D+3.33 D=2.58 D.
Not Possible:
addition refraction=2.00 D;
refraction distance near=40 cm;
principal viewing distance near=20 cm;
IZ=2.00 D−2.50 D+5.00 D=4.50 D In the calculation, it is assumed that no change of the amplitude of accommodation due to the change of the near distance occurs. However, this merely represents an approximation.

The graphical user interface 120 shown in FIG. 5 further comprises a section or input field "Base Curve" (section 135) into which the base curve fitting the selected frame best can be entered. In particular, it is possible to input a deviating base curve depending on the bending of the spectacles frame and to consider it in the optimization of the spectacle lens. The program automatically calculates the best-suitable bending or base curve for the respective refraction data and the respective base curve needs. The base curve calculated by the program may differ from the base curve input into the input field "Base Curve". Preferably, the input or ordered base curve is checked automatically as to that no plane and convex surface on the backside or rear surfaces curved to strongly arise, which may in particular cause too high an edge thickness.

FIG. 6 shows a mask or graphical user interface 140 for inputting individual data relating to the current, so far worn spectacles.

Information on the previous lenses can be entered into this mask, if known. For example, it can be selected from a list 142 ("lens type") whether the customer had single-vision, multifocal or progressive lenses or whether it is the first spectacle lens of the customer (no previous spectacle lenses). If progressive lenses were worn, further information on e.g. the material, the refractive power and/or the progression length may be made e.g. in a pop-up menu. Furthermore, the progression length of the previous spectacle lenses can be input automatically on the basis of the selected previous product, or manually. In particular, the progression length of the previous spectacle lenses may roughly be classified as e.g. a "standard" or long progression or as a short ("XS") progression length.

If the addition of the previous lenses is known, it can be entered into a dedicated input field 144 "Addition of the Previous Lenses". Thus, the addition of the previous lenses can be compared to the new addition. In the case of an addition increase of more than 0.5 D, a note field (e.g. as a pop-up window) may come up, which points out to the particularities of the addition increase.

FIG. 7 shows an example of a mask or graphical user interface 146 ("Design Profiler") for inputting data relating to the individual preferences and weighing of the viewing zones.

Five different pictographs for the distance, intermediate distance and near as well as the active behavior of the spectacle wearer each symbolize the zones the spectacle wearer should weigh up when choosing their design profile. The pictographs serve as examples of the respective distance zone and only represent a small selection of possible activities for that distance. With the points to be allocated, the zones can be weighted.

In a specific example, a total of 9 points can be allocated to the four different zones (distance, intermediate distance, near and active behavior). The more important the respective distance zone is to the customer and the more of their activities fall into a zone, the more points are allocated for this zone. The number of points per zone and the overall number can be restricted. For example, a maximum of 5 points may be allocated to one zone, but not more than 9 in total.

The allocated points determine the spectacle wearer's individual design profile. Expressed in simplified terms: The more points are allocated to the distance in relation to the given overall points, the lower is the individual distance reference point, and the more points are allocated to near in relation to the overall points, the higher is the individual near reference point. The points for the active behavior and the intermediate-distance vision mainly influence the length of the progression zone and thus also determine how distortion-free the spectacle lens is. An allocation of the same number of points to each zone corresponds to a balanced, universal design.

Figure 8:
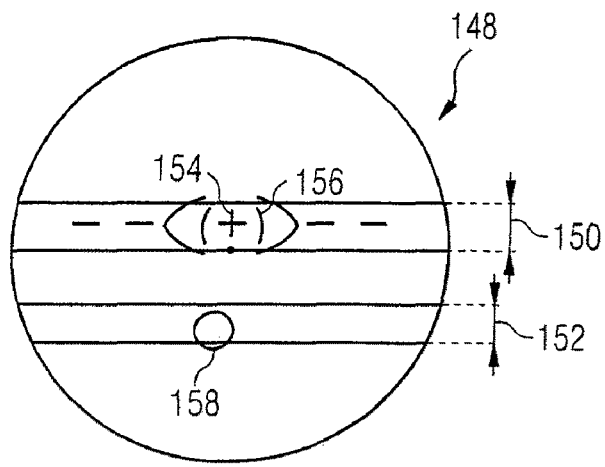
FIG. 8 a schematic illustration of the positions of the distance and near reference points of an individual spectacle lens design.

FIG. 8 shows the positions of the distance and near reference points of an individual spectacle lens design 148. The zones (150 and 152) in which the distance reference point (zone 150) and the near reference point (zone 152) can preferably be found have a gray background. The position of the centration and/or fitting point is marked by means of a cross 154 (centration cross). The distance reference point is in the middle of two round brackets 156. The near reference point is in the middle of the near measuring circle 158.

The vertical height of the distance reference point can preferably be determined flexibly, depending on the individual data of the spectacle wearer, in a range between +4 to −4 mm with respect to the centration and/or fitting point set for this spectacle lens by the manufacturer. The near distance point can preferably be determined flexibly between 13 and 20 mm vertically below the centration and/or fitting point. This results in a flexibly selectable progression length, which may preferably have a minimum of 13 mm and a maximum of 24 mm. Preferably, the distance and near reference points can be freely determined in steps of 0.1 mm within an admissible range. If e.g. the distance reference point is shifted to a vertical height of and/or −4 mm, the near reference point has to at least be at a vertical height of −17 mm. If the distance reference point is shifted to +4 mm, a minimum progression length of 17 mm results, since the near reference point preferably is not shifted to more than −13 mm.

The minimum vertical distance from the lower frame edge to the near reference point is preferably 2 mm. The distance reference point preferably has a minimum vertical distance of 6 mm, preferably of 8 mm from the upper frame edge. The maximally admissible progression length can be calculated with the help of the minimally admissible distances of the distance and near reference points from the upper and lower frame edge, respectively. The progression length is defined as the vertical distance between the distance reference point and the near reference point.

The effects achieved by shifting the design point in the progressive lens can be taken from the following table:

TABLE

| Individual vision needs of the spectacle wearer | Implementation during determination of the positions of the design points |
| --- | --- |
| Particularly large distance zone, e.g. driver | The design point "distance" should be shifted below the centration cross. The progression zone then only (clearly) begins below the centration cross. |
| Particularly large near zone, e.g. editor | The design point "near" should be shifted upward compared to the previous progressive lens. This allows for a relaxed near vision with a comfortable infraduction at the same time. |
| Particularly wide progression zone, e.g. architect | The design point "distance" should be shifted upward and the design point "near" downward. The longer the progression zone, the wider the progression corridor and the less rocking motion the customer notices. |

The positions of the distance and near reference points are preferably the same for the right and left spectacle lenses. However, in the case of different visual heights, the viewing zones of one of the eyes may be negatively affected. In order for the viewing zones of both eyes to be fully used, it is advantageous to select and determine the respective smaller vertical distance of the near reference point from the centration point.

Figure 9:
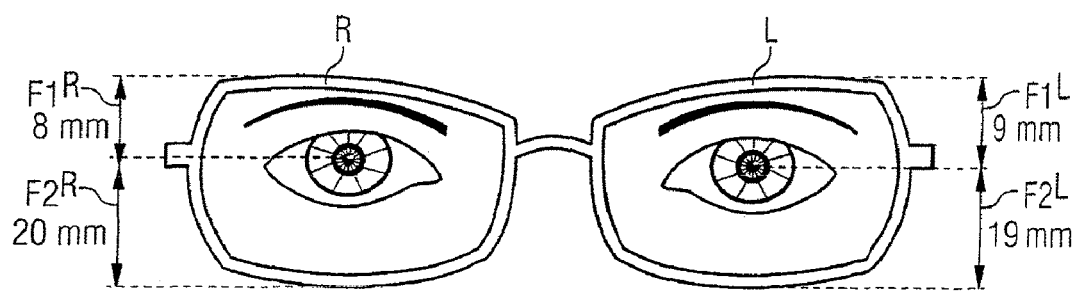
FIG. 9 an example of different visual heights of the two eyes.

FIG. 9 explains this relation. In FIG. 9:
$F1^{L,R}$ designates the vertical distance "centration point–upper frame edge" of the left (L) and the right (R) spectacle lens; and
$F2^{L,R}$ designates the vertical distance "lower centration point–lower frame edge" of the left (L) and the right (R) spectacle lens.

In FIG. 9, the centration point and the distance reference point coincide. If the selection of the suitable vertical position of the near reference point is made on the basis of the lower frame edge, a vertical distance of the near reference point from the centration point of −18 mm would result for the right eye, and said distance would be −17 mm for the left eye. In this case, it is preferred to select and determine the smaller distance.

The data on the object distances "distance" and "near" in the refraction determination are taken into account in the calculation and optimization. Thus, the beam path corresponding to the actual situation of wear can be simulated more precisely and the imaging quality can consequently be improved.

Figure 10A:
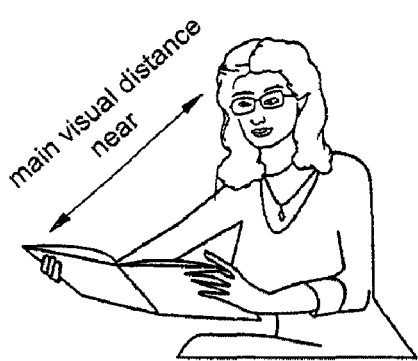
FIG. 10a,b a schematic illustration of the principal viewing distance near (FIG. 10a) and the refraction distance near (FIG. 10b)
Figure 10B:

In particular, it is possible to take the principal viewing distance in near vision in the actual position of wear of the spectacle lens into account when calculating the lens. FIG. 10a illustrates the principal viewing distance in near vision in the actual position of wear of the spectacle lens and FIG. 10b the refraction distance near or near distance in the refraction determination.

Generally, it is assumed that the addition has been determined in a near refraction distance of 40 cm (applies to additions up to 2.50 D, for higher additions, 1/addition holds true) and that it corresponds to a principal viewing distance in near vision of 40 cm. If the principal viewing distance in near vision deviates for the near refraction distance, the individual spectacle lens design can be optimized for this principal viewing direction.

When the optimum individual position of the distance and/or a near reference point is determined on the basis of individual data of the spectacle wearer, a corresponding spectacle lens design with the thus determined positions of the distance and near reference points, and optionally considering further individual parameters of the spectacle wearer, is automatically calculated.

Figure 11:
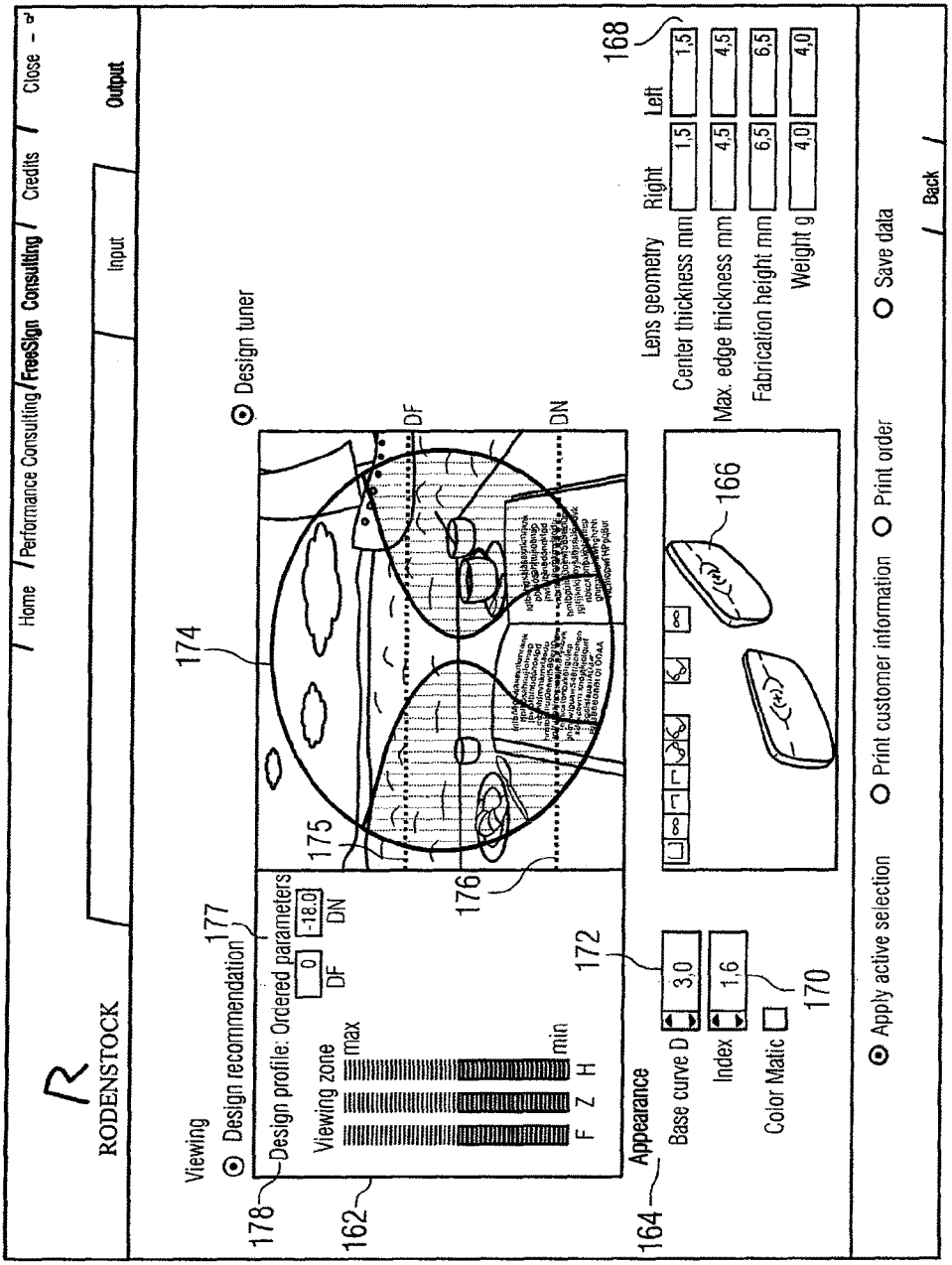
FIG. 11 an example of a graphical user interface for the representation of results.

As shown in FIG. 11, the design proposal can be visualized by means of a suitable graphical user interface 160A in order to represent the result (design recommendation). Depending on the selection in the settings, an additional graphical user interface 160B (design tuner) may be shown (cf. FIG. 12) with which, in addition to a result representation, the user is given the possibility to actively change the design by changing the individual position of the distance and/or a near reference point and/or by changing the individual data of the spectacle wearer (in particular the preferences, the frame data, etc.). In addition, the corresponding geometric data of the spectacle lens (center thickness, edge thickness, base curve, weight) can be calculated and be visualized as well by means of a suitable graphical user interface (preferably in the form of a three-dimensional module).

The graphical user interfaces 160A and 160B are divided into two areas: In the upper area 162, information on "Viewing" and/or "Performance" with the proposed individual spectacle lens design are illustrated; in the lower area 164, information on "Appearance" and "Geometry" of the individual spectacle lens or spectacles are illustrated.

In the area "Appearance" 164, in particular cosmetic properties and data regarding the aesthetics of the spectacle lens (e.g. weight, geometric data, such as fabrication height, maximum edge thickness, center thickness, base curve, etc.) of the edged spectacle lens(es) can be visualized and graphically illustrated. The visualization of the cosmetic properties of the spectacle lens may e.g. be achieved by means of a three-dimensional graphical representation of a model of the spectacle lens 166 with the determined geometric data, as is e.g. shown in FIGS. 11 and 12. The representation of the cosmetic properties of the spectacle lens may be influenced by selection of the base curve and the refractive index. The selection may depend on the effect.

Furthermore, the area "Appearance" 164 may comprise a sub-area 168 in which numerical values relating to the geometric properties of the spectacle lens, such as fabrication height, maximum edge thickness, center thickness, weight, base curve of the edged lens, etc. are shown. These values may be approximate values which optionally deviate from the actual lens geometry data. In addition to the engravings, individually determined distance and near reference points may be shown as marking points.

Views 169 of the edged spectacle lenses can be shown from different static perspectives (frame from above, frame from the front, from the side, from diagonally above) by means of suitable buttons. Moreover, the edged spectacle lenses can be made to rotate dynamically in the selected view by pressing an animation button. For a more detailed view, the image may be enlarged by means of a corresponding button.

Furthermore, the area "Appearance" 164 comprises a section 170 for displaying numerical values relating to the refractive index and a section for displaying the base curve (section 172). The displayed values for the base curve and the refractive index are composed of the effect range, the necessary diameter, the base curve wish, and the refraction data. Therefore, deviations from the base curve wish input into the mask "Ordered Values" are possible. The technically realizable values for the base curve and the refractive index of the lens can be changed via corresponding selection fields. If changes of the default base curve, the refractive index, etc. are made, the graphical illustration and the geometric data can be calculated again according to the changed values by pressing the button "Refresh".

In addition to the visualization of the cosmetic properties of the spectacle lens, a visualization of the optical properties of the spectacle lens takes place (viewing zones, in particular spatial location and size of the individual viewing zones). The representation of the sizes of the viewing zones can merely take place relative to the prescription data without taking a possible material dependence into account. Of course, consideration of a material dependence may be provided for. In addition to a visualization of the "Appearance", a visualization of the "Viewing" through the spectacle lens takes place as well. In particular, a visualization of the viewing comfort (e.g. infraduction, rocking, peripheral vision, distortions, etc.) may be provided for.

In addition, a suitable representation of performance values relating to the viewing zones, the viewing comfort and/or the cosmetic properties and the aesthetics of the individual spectacle lens may be provided for. Furthermore, performance values of alternative design proposals may be represented as well.

The area "Viewing" 162 of the graphical user interfaces 160A and 160B is therefore always divided into several sub-areas.

In the sub-area 174 "Binocular Viewing Zone Representation" of the area 162, the design ideal for the customer and the specified frame is schematically shown by means of an ellipsis. Gray areas are areas with aberrations (e.g. astigmatism in position of wear larger than 0.5 D). Moreover, the course of the 0.5-D isoastigmatism line may optionally be shown. The vertical heights of the distance and near reference points may each be characterized by (optionally differently colored) lines 175, 176. In the sub-area 177 of the area 162, numerical values for the spatial positions (in particular for the vertical height with respect to the centration point) of the distance and near reference points are shown.

In the sub-area 178 "Design Profile" of the area 162, a qualitative comparison of the sizes of the viewing zones with respect to each other is illustrated e.g. in the form of bars of different lengths, wherein F designates the distance zone, Z the intermediate zone, and N the near zone. The length of the respective bar or slide correlates with the respective setting of priorities associated to a corresponding distance zone. Since the length in the design profile results from the values of all previous masks, it may deviate from the preferences and weightings made by the customer before. Moreover, a qualitative assessment of the dynamic visual impression through the individual spectacle lens can be represented. The higher the bar representing the dynamic visual impression (bar "Dynamics"), the longer the progression zone length and the more the spectacle lens resembles a single-vision lens and the less rocking effect the spectacle lens has.

In addition, the optician and/or the spectacle wearer may be given the possibility to actively change the thus calculated spectacle lens. The change is e.g. made by actively altering the spatial position, in particular the vertical height of the distance and/or a near reference point. Alternatively, the weightings of the viewing zones can be changed.

Figure 12:
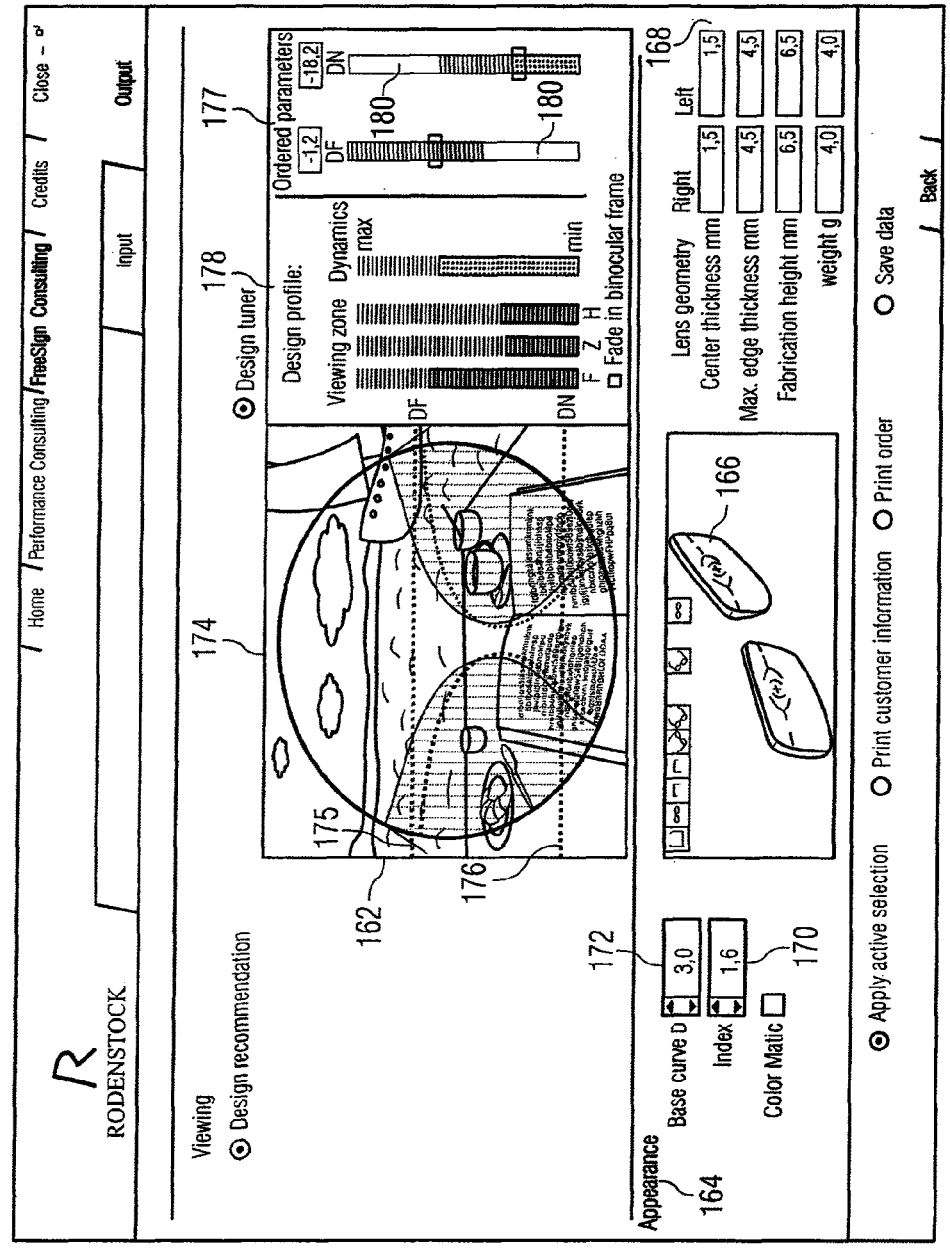
FIG. 12 an example of a graphical user interface for the representation of results and design modification or tuning.

The change or adaptation of the position of the distance and/or a near reference point and/or the preferences with respect to the viewing zones can e.g. be done by means of a graphical user interface. An example of a suitable graphical user interface in the form of a slide control 180 is shown in FIG. 12. By means of the slide control 180 shown in FIG. 12, a direct adaptation of the position of the distance and/or a near reference point is possible.

The new spectacle lens design with the changed position of the distance and/or a near reference point is preferably calculated and visualized in real time. Preferably, the difference or change of the optical properties of the new spectacle lens design with respect to the old one is visualized as well.

In addition to the possibilities described in the design recommendation (FIG. 11), an ellipse may e.g. be faded in in the design tuner, which in the box dimensions and the specified centration corresponds to the approximate, binocular customer frame. Furthermore, the proposed, individual design can be changed here by e.g. sliding slide controls for the distance and near reference points upward or downward. In the ordered parameters in the display fields for the distance and near reference points, the numerical values for the positions of the reference points change correspondingly. Moreover, the lines for the distance and near reference points shift in the binocular viewing zone representation as well.

In addition to the gray viewing zones of the design recommendation, preferably colored (e.g. yellow) viewing zone lines (e.g. 0.5-D isoastigmatismline) may appear, which illustrate the altered, individual design. Also, in the sub-area design profile 178, the relation of the sizes of the viewing zones with respect to each other and the length of the bar "Dynamics" change as well. The allocated points in the section "Design Profiler" are preferably not influenced by the changes in the section "Design Tuner".

The following examples show individual progressive design with distance and near reference points determined individually depending on the obtained individual data of the spectacle wearer.

Example 1

Spectacle Wearer Architect

The spectacle wearer attaches great importance to a wide intermediate zone and wishes to have a rather "quiet spectacle lens" with little rocking motion, since most of the day he uses the intermediate zone (medium distance) for job-related reasons. With his current spectacles he wears a progressive lens with a progression zone length of 18 mm.

For this spectacle wearer, for the selected frame and corresponding centration, the program suggests setting the distance reference point at +2.4 mm above the centration and/or fitting point. Optimally, the near reference point would be at −19 mm below the centration and/or fitting point. With this progressive spectacle lens, the architect has a good compromise of a relaxed head posture, a wide intermediate zone, and little rocking motion for his viewing habits.

Example 2

Spectacle Wearer Editor

She attaches great importance to a large near zone and wishes to have to lower her view less than with her current spectacle lens, since most of the day she spends working in the near zone for job-related reasons. With her current spectacles he wears a progressive lens with a progression zone length of 18 mm. For this spectacle wearer, for the selected frame and corresponding centration, the program suggests setting the distance reference point at 1.5 mm above the centration and/or fitting point. Optimally, the near reference point would be at −15.5 mm below the centration and/or fitting point. Thus, the editor has a good compromise of a wide near zone and a relaxed head posture.

If the spectacle wearer attaches great importance to wide intermediate and near zones and little rocking motion in the spectacle lens, the program suggest shifting the distance reference point upward depending on the other input parameters. The distance reference point would then be above the centration and/or fitting point. Depending on the refraction data and the individual parameters, a "blurring" in the centration and/or fitting point of up to +0.25 D can arise. In addition to this slight blurring in the centration point, lateral restrictions in the distance zone can occur as well, since the spectacle wearer—when the distance reference point is shifted upward—looks in the zero direction of sight due to the progression in the spectacle lens beginning earlier. Due to the changed position of the progression zone in the spectacle lens, the viewing zones may be accordingly smaller at the level of the centration point, since the peripheral aberrations are shifted "upward". However, when selecting the position of the distance reference point, the spectacle wearer obtains a spectacle lens design or spectacle lens designed and optimized according to their individual viewing habits.

Example 3

Spectacle Wearer Works in the Field

The spectacle wearer attaches particular importance to a large distance zone, since most of the day he uses the distance zone for job-related reasons. With his current spectacles he wears a progressive lens with a progression zone length of 18 mm. For this spectacle wearer, for the selected frame and corresponding centration, the program automatically calculates and suggests setting the distance reference point at −2.5 mm below the centration and/or fitting point. Optimally, the near reference point would be at −18.4 mm below the centration and/or fitting point. With this progressive spectacle lens, the spectacle wearer has a large distance zone and a good compromise of little rocking motion and well usable intermediate and near zones.

Example 4

Following the question as for which activities and vision needs the spectacle wearer uses their spectacles, the following profile results for example:
  she drives a car regularly and watches TV;
  she plays an instrument and attends an orchestra rehearsal 2 times per week;
  in the evening, she likes reading the daily newspaper;
  she does sports at least 1 time per week, e.g. jogging or playing handball in a club.

In her current spectacles, she wears progressive lenses with a normal progression zone length. Since no preferences can be seen and the activities of this customer are equally distributed to the zones distance, medium distance and near, the same number of points is allocated to all distances and also to the activity behavior or dynamics. In other words, all viewing zones and the dynamic behavior or the dynamic characteristics are weighted equally. In the specific example, 2 points are allocated for all zones of the "Design Profiler" shown in FIG. 7. In the graphical user interface "Design Recommendation", the calculation result is displayed considering the individual inputs into the previous masks. The program automatically calculates and suggests positioning the distance reference point at 0 mm and the near reference point at −18 mm for this customer. This spectacle lens would correspond to a balanced, universal progressive spectacle lens having a progression zone length of 18 mm (e.g. a spectacle lens "Impression ILT®" by the company Rodenstock GmbH), since when choosing the design, it is assumed that there is no emphasis on any activity in one of the distance zones.

Example 5

Following the question as for which activities and vision needs the spectacle wearer uses their spectacles, the following profile results:
  he attaches particular importance to an undisturbed distance vision, since he spends most of the day in the car for job-related reasons;
  he only needs medium distance vision in order to clearly see the dashboard;
  near vision is only required for short writing activities, such as conclusions of contracts and the like;
  in this leisure time, he likes playing tennis and squash; little rocking motion in the spectacle lens is of particular importance to him.

In his current spectacles, he wears progressive lenses with a normal progression zone length (PZL). The spectacle wearer's preference is clearly the distance vision; the medium distance and the near play a subordinate role. Therefore, in this example, 4 points were allocated to the distance, and 1 point for medium distance and near each (cf. FIG. 7). Due to the requirements of the dynamic sports, such as freedom of distortion and good spatial perception, the activity behavior or dynamics was weighted with 3 points in the "Design Profiler" shown in FIG. 7. In the graphical user interface "Design Recommendation", the calculation result is displayed considering the individual inputs into the previous masks. The program automatically calculates and suggests positioning the distance reference point at −1.1 mm and the near reference point at −18.5 mm for this customer. Due to the position of the near reference point and the related relatively long progression zone length, the spectacle lens resembles a single-vision lens and is almost distortion-free. This influences the sporting activities of the spectacle wearer in a positive manner.

Example 6

Following the question as for which activities and vision needs the spectacle wearer uses their spectacles, the following profile results:
  distance vision plays a subordinate role, since he usually takes the spectacles off when driving a car;
  medium distance vision is of particular importance to him;
  the spectacle wearer is very sensitive to unusual distortion, e.g. in the case of curved lines in his graphical sketches;
  after work, he likes reading detective stories;
  due to his stressful job, he has no time for sports or other activities.

Thus, the most important distance for this spectacle wearer is the medium distance, near vision is important as well, distance vision and activity behavior play a subordinate role. Therefore, in the "Design Profiler" shown in FIG. 7, 1 point is allocated to the distance vision and the activity behavior each, 3 points for the medium distance and 2 points for the near vision. In the graphical user interface "Design Recommendation", the calculation result is displayed considering the individual inputs into the previous masks. The program automatically calculates and suggests positioning the distance reference point at +0.7 mm and the near reference point at −18.5 mm for this customer. Thus, the largest possible intermediate zone is realized. Due to the position of the near reference point and the related relatively long progression zone length, the spectacle lens resembles a single-vision lens and is almost distortion-free. This is of benefit to the spectacle wearer during his work with graphical sketches.

Example 7

Following the question as for which activities and vision needs the spectacle wearer uses their spectacles, the following profile results:
  she hardly uses the spectacles for distance vision activities, it therefore plays a subordinate role;
  reading documents is particularly important in her job;
  she attaches great importance to a comfortable infraduction for near vision tasks;
  due to the rather static posture at the workplace, rocking motions play a subordinate role;
  medium distance vision is necessary for occasional computer work.

The most important distance for this spectacle wearer is the near distance. The medium distance is important as well, distance vision and the activity behavior play a subordinate role. Therefore, in the "Design Profiler" shown in FIG. 7, 4 points are allocated to the near vision, 2 points for the medium distance and 1 point for the distance vision and the active behavior each. In the graphical user interface "Design Recommendation", the calculation result is displayed considering the individual inputs into the previous masks. The program automatically calculates and suggests positioning the distance reference point at +0.8 mm and the near reference point at −17.0 mm for this customer. Thus, the largest possible intermediate and near zones are realized for the customer's needs. Due to the position of the near reference point, the spectacle wearer's wish for a comfortable infraduction for near vision tasks is put into practice in her individual progressive lens.

With a button "Apply Active Selection", it can be determined which data are to be applied for the order. For example, the data for the area presently active (not in the background) are always applied. After the button "Apply Active Selection" has been pressed, an order form filled with the result can be printed out. The order form may be completed e.g. with further details, such as color, coating, ColorMatic color, measuring frame, etc. The individual data can also be stored and/or sent online to a spectacle lens manufacturer.

The individual data of the spectacle wearer can also be obtained by means of suitable order forms and be forwarded to the spectacle lens manufacturer. FIG. 13 shows an exemplary order form. In the order form are indicated the obtained individual refraction data (sphere, cylinder, axis, prism, base), frame and centration data, individual parameters of the spectacle wearer's eyes and the individual position of wear (pupillary distance, face form angle, forward inclination, corneal vertex distance, etc.), and optionally further individual data. With the help of the order form, it is possible to select the positions of the distance and/or a near reference point such that these correspond to the positions of a universal progressive lens design (e.g. Impression® or Impression XS® by the company Rodenstock GmbH). It is also possible to specify a medium progression zone length of 16 mm. Alternatively, the positions of the distance and/or a near reference point may be specified depending on the individual frame data (frame-optimized design). In this way, for example, the distance reference point can be specified on the centration point (i.e. at 0 mm) and the near reference point at 2 mm above the lower frame edge. Furthermore, the positions of the distance and near reference points can be determined individually considering further individual data (e.g. emphasis on activities and preferences regarding the viewing zones), as has been explained in detail above.

Subsequently, an individual spectacle lens is calculated and optimized, wherein the optimization takes place considering at least part of the obtained individual data, in particular data regarding the individual parameters of the spectacle wearer and the individual position of wear (face form angle, forward inclination, pupillary distance, corneal vertex distance, etc.).

In order to describe and/or calculate the imaging properties of spectacle lenses in the situation of wear, two calculation methods are known in geometrical optics:
calculation with light rays (ray tracing); and
calculation with wave fronts (wave tracing).

The term "ray tracing" is comprised of ray (German: Strahl) and tracing (German: Verfolgung). In geometrical optics, the ray tracing method is used to describe optical imaging. However, the calculation of a spectacle lens by means of ray tracing is very time-consuming, since for each point in the spectacle lens except for the actual light ray or main ray an "accompanying" bundle of neighboring rays through the spectacle lens has to be simulated as well.

Preferably, the individual spectacle lens is calculated by means of a wavefront tracing method, in particular by means of a local wavefront optimization. The term "wave tracing" is comprised of wave (German: Welle) and tracing (German: Verfolgung). Wavefronts can be used like light rays to describe or calculate optical imaging. A wavefront is the surface of same phase of a propagating wave. Each such wavefront combines all properties of a bundle of neighboring rays in a single object. Thereby, the calculation time can be reduced considerably, so that an individual optimization of each single spectacle lens is enabled. In particular, due to the free selection of the design points distance and/or near, it is possible to tailor the distribution of the imaging properties on the spectacle lens to the individual viewing habits of the spectacle wearer.

Figure 14:
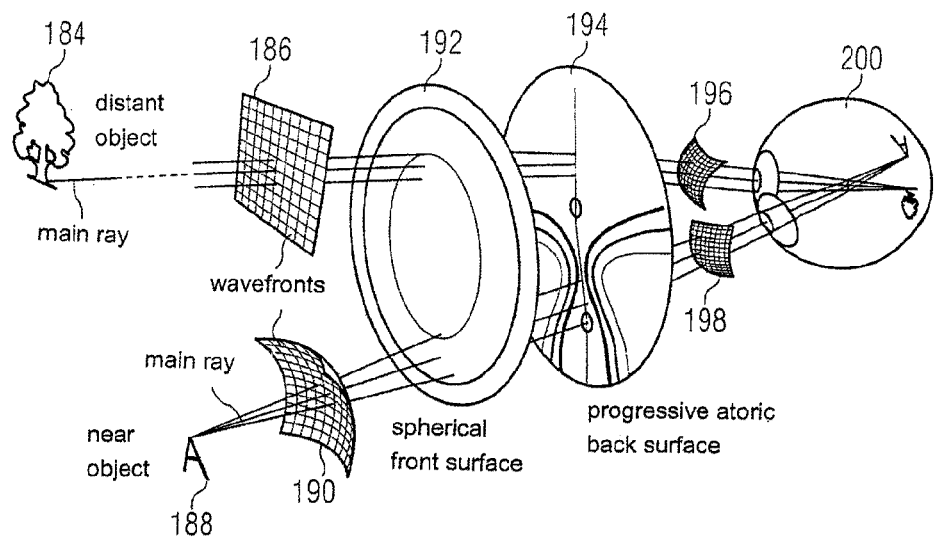
FIG. 14 a schematic illustration of the physiological and physical model of a spectacle lens in a specified position of wear.

FIG. 14 shows a schematic illustration of the physiological and physical model of a spectacle lens in a specified position of wear, which it can be seen in FIG. 13 that the rays from an infinitely distant object 184 are all parallel, which is reflected in a plane wavefront 186. In contrast, the rays coming from a near object 188 diverge. The wavefront 190 is curved accordingly. The spectacle lens having a preferably spherical front surface 192 and an individually calculated, progressive atoric rear surface 194 now has to make sure that each wavefront 196, 198 is curved on the eye side such that the corresponding object 184, 188 is sharply defined on the retina of the eye 200. In an ideal case, these wavefronts must be curved on the eye side to the same extent for all directions of sight.

For the calculation of the spectacle lens, use is preferably made of a flexible surface design of the progressive surface to be calculated individually, having a plurality of evaluation points (preferably more than 7000 evaluation points), wherein each of these evaluation points is assigned its own local wavefront tracing. Preferably, the individual progressive surface is optimized by minimizing a target function evaluated at the evaluation points and by taking the physiological vision model into account. In this manner, it is possible to perform the optimization of a spectacle lens according to the variable target function by means of individual wavefront tracings very quickly and thus online after receipt of order.

The calculation of the spectacle lens preferably comprises an optimization with more than 2000 optimization parameters in a highly dimensional space. Multiprocessor mainframe computers can be used for the thus performed real-time online optimization.

Preferably, in the individual optimization of the spectacle lens, not only aberrations of low order (sphere, cylinder, prism), but also aberrations of higher order (e.g. coma and spherical aberration) are minimized. In this respect, reference is made to U.S. Pat. No. 7,063,421 B1. The fabrication of the individually calculated spectacle lens takes place e.g. by means of precision machines, preferably CNC grinding and polishing machines capable of realizing the calculated surface data with a precision in the μm range.

Preferably, in the optimization of the individual spectacle lenses, Listing's rule is particularly taken into account.

Figure 15A:
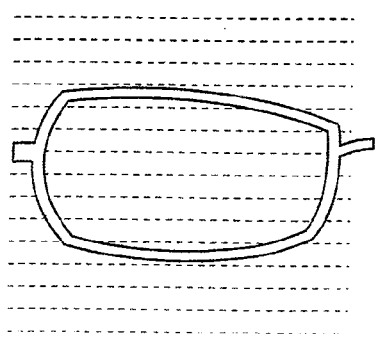
FIGS. 15a,b schematic illustrations of the axis positions in a spectacle lens without taking Listing's rule into account (FIG. 15a) and with Listing's rule considered (FIG. 15b)
Figure 15B:
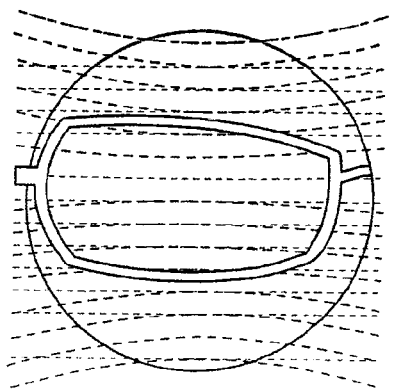

FIGS. 15a and 15b are schematic illustrations of the axis positions in a spectacle lens without taking Listing's rule into account (FIG. 15a) and with Listing's rule considered (FIG. 15b).

Since the eye performs a slight cycloduction during peripheral sight deviations, or eye excursions, there must not be a fixed cylinder axis throughout the entire spectacle lens, but it must change in the transition from the horizontal to the vertical (FIG. 15b). If the cylinder (known due to refraction) present in the eye is to be corrected well by the spectacle lens, the axis position of the cylinder in the spectacle lens must match well with the axis position the eye actually assumes because of its cycloduction. If the axis positions of the eye and the spectacle lens do not match, two obliquely crossed cylinders result. In the case of oblique, lateral sight deviations, the spectacle wearer would have an astigmatism that would not be corrected. This leads to a loss of vision in one zone. Preferably, the torsion adjustment is considered in the calculation of the individual spectacle lens. The consideration of Listing's rule becomes all the more relevant:
the higher the refraction cylinder of the customer is, and/or
the stronger the sight deviation deviates from the horizontal and vertical excursion, and/or
the stronger or larger the sight deviation is in total.

In a conventional progressive spectacle lens with a progressive front surface and a spherical/toric prescription surface, Listing's rule cannot be applied—in contrast to spectacle lenses with a progressive, individual, eye-side freeform surface.

Further preferably, in the optimization and calculation of the individual progressive spectacle lens, an individual predecentration is taken into account. Thus, the usable diameters are enlarged. The optimum predecentration can be calculated automatically on the basis of data relating to the frame and spectacle lens shape and data relating to the centration. Alternatively, an individual predecentration can be set by the optician himself. In this case, the desired diameter determined by means of a special centration card can be taken into account as well. In particular, a predecentration of up to 5 mm can be considered.

The individually calculated spectacle lens preferably has a spherical or rotationally symmetrical, aspherical, object-side front surface and an individual, progressive, eye-side freeform surface optimized depending on individually determined reference or design points distance and near, the individual refraction data, the individual parameters of the spectacle wearer and the situation of wear (e.g. pupillary distance, forward inclination, face form angle, corneal vertex distance, etc.).

The positions of the individual distance and near reference points are preferably marked by means of an individual stamping by means of non-permanent markings. Preferably, the positions of the individual distance and near reference points can be uniquely reconstructed by means of permanent markings or micro-engravings of the spectacle lens and a reconstruction rule (template, centration card).

FIGS. 16a, b show examples of non-permanent stampings of two individual progressive spectacle lenses.

The non-permanent marking or stamping of an individual spectacle lens optimized according to a preferred method of the invention consists of "movable" and "fixed" parts. The movable parts include two round brackets 202 marking the position of the distance reference point or the design point distance, and the near measuring circle 204 which marks the position of the near reference point or the design point "near". The distance reference point is located in the middle of the round brackets 202 and the near reference point in the middle of the near measuring circle 204. Depending on the positions of the distance and near reference points, the stamping of an individual spectacle lens may look differently thus. The position of the centration and/or fitting point is marked by means of a cross 206 (centration cross).

In a normal case, the prism reference point 208 is located 4 mm below the centration point. If the anisometropia is higher and the customer has a certain wish regarding a specific weighting (e.g. if the prismatic vertical differences are to be matched in the near zone), a prism matching point can be shifted in the desired direction.

In the example shown in FIG. 16a, the distance reference point is located at the level of the centration point. The near reference point is located at a vertical level of −18 mm below the centration point. FIG. 16b shows a further example of an individual stamping or an individual stamping image of an individual spectacle lens. The spectacle lens is individually calculated and optimized for a spectacle wearer attaching great importance to a large distance zone. The distance reference point is located at a vertical level of −4 mm below the centration and/or fitting point and the near reference point is located at a vertical level of −18 mm below the centration and/or fitting point.

Preferably, the values for the positions of the distance and near reference points (in particular for the vertical level with respect to the centration and/or fitting point) are also permanently engraved in the spectacle lens.

In exceptional cases, the stamping may differ from the above-described one. Furthermore, an explicit, non-permanent marking of the positions of the distance and near reference points and/or the centration and/or fitting point may be omitted. However, the reference points can be uniquely determined by means of a reconstruction rule comprising a centration card, stamped scales in steps of 1 mm, and a lens packet. In order to reconstruct the reference points, the spectacle frame is put onto the centration cross of the centration card with the marked centration point and the positions of the distance and near reference points are drawn onto the spectacle lens. The positions of the distance and near reference points may also be determined with the help of the permanently engraved values below the nasal base curve and index engravings.

In addition to a reconstruction of the positions of the reference points, it is possible to determine an optimum diameter of the raw-round spectacle lens by means of a corresponding centration card.

The determination of an optimum diameter by means of a centration card can be performed as follows:

1) Determining the corresponding minimum diameter for the selected frame, which—irrespective of the lateral centration—corresponds to the smallest circumscribing diameter circle of the centration card. This value corresponds to the first value in a diameter order, e.g. 50/60.

2) Positioning the visual point determined in the fitting process on the centration card such that it coincides with the centration cross of the centration card.

3) Reading the largest required diameter. In a decentration in the nasal direction, which is mostly the case (pupillary distance PD smaller than the center distance of the frame), this is the diameter circle which temporally circumscribes the frame. This value corresponds to the second value of the diameter order, e.g. 50/60. Preferably, the difference between the usable diameter and the minimum diameter is not more than 10 mm.

4) If the diameters are nasally and temporally equal, a centric version of the order is recommended.

In addition to the non-permanent markings or stampings, the individual spectacle lens also has permanent (micro-) engravings.

FIG. 17 shows the permanent engraving of an individually optimized, left spectacle lens viewed from behind (i.e. from the eye side). The functional engraving or permanent marking for the alignment of the spectacle lens is the infinite sign. The two functional engravings 210, 212 are located at a mutual distance of 34 mm at the level of the centration point or centration cross. Below the nasal infinite sign 212, the base curve engraving 214 and the index engraving 216 are located, both having two digits. Therebelow is the engraving 218 for the positions of the distance and near reference points. The first number indicates the vertical distance of the distance reference point relative to the centration and/or fitting point. The second number indicates the vertical distance of the near reference point relative to the centration and/or fitting point.

The distance reference point may preferably be in a range between −4 and +4 mm below or above the centration point. The near reference point may preferably be in a range between −13 and −20 mm below the centration and/or fitting point.

The two-digit addition engraving 220 is located temporally below the functional engraving 210.

In summary, in FIG. 17 designates:

| | |
|---|---|
| ∞ | functional engraving; |
| 25 | addition; |
| 65 | base curve; |
| 60 | refractive index; |
| −4 | individual vertical distance of the distance reference point from the centration and/or fitting point; |
| 18 | individual vertical distance of the near reference point from the centration and/or fitting point. |

The finished and stamped spectacle lens is packed into a lens packet and supplied to the optician/customer. An example of a lens packet is shown in FIG. 18. FIG. 19 shows a list of the pictograms and symbols used on the lens packet.

The individual data of the spectacle wearer are printed on each lens packet. More specifically, the following data are printed on each lens packet:

lens type, material, color, coating, diameter ordered values: sphere, cylinder, axis, prism (resulting), base (resulting), addition;

target measured values for the focimeter in the measuring point for distance and addition in a concave vertex measuring position incl. the measurable prism in the prism reference point (composed of DRP and ordered prisms);

with prismatic refraction data: information on the type of refraction: PD centration (PMZ) or equation case (FF) and size and direction of the necessary centration correction;

general order data, additional information and commission on the back of the lens packet;

information on the individual parameters: monocular PD, CVD, FI, FFA;

information on the design points: positions of distance and near reference points with respect to the centration and/or fitting point;

base curve, predecentration and inset of the lens; indication of the corrected PD for fitting (COR PD) if the lens shape and the centration data are known.

The lens packet particularly contains the relevant data for a correct fitting in the spectacle frame, in particular data relating to the frame and lens shapes.

In particular, in an order where the lens shape and the centration data are indicated (such as with sports eyewear), the corrected pupillary distance PD is calculated for fitting (COR PD). This is necessary in order to obtain the right customer PD in the spectacles already provided with lenses. Also in the case of spectacle lenses with correction prism, the COR PD is to be used for fitting instead of the customer PD if the shape has been indicated. The necessary centration correction for prisms with horizontal and vertical base positions has already been taken into account in the calculation of the spectacle lenses. Thus, the value for the centration correction on the lens packet is always zero.

In an order without shape indication, the COR PD cannot be calculated, since the parameters (frame and centration data) required for the calculation thereof are not transmitted. In progressive spectacle lens with correction prisms optimized individually according to a preferred optimization method, the centration correction for prisms with horizontal and vertical base positions is preferably taken into account already when the lenses are calculated. The value for the centration correction on the lens packet remains zero. In an order where no shape is indicated, this value relates to the PD.

Figure 20A:
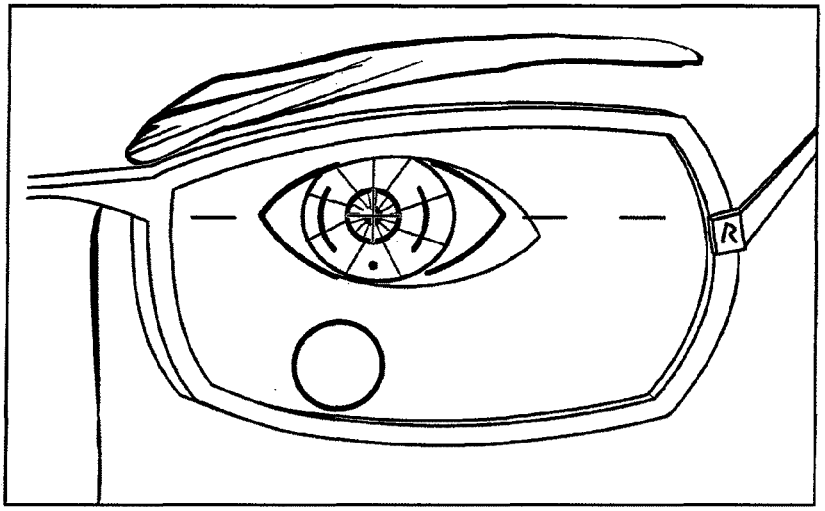
FIGS. 20a,b examples of the centration of an individual spectacle lens (FIG. 20a) or a standard spectacle lens (FIG. 20b) in front of the wearer's eyes.
Figure 20B:
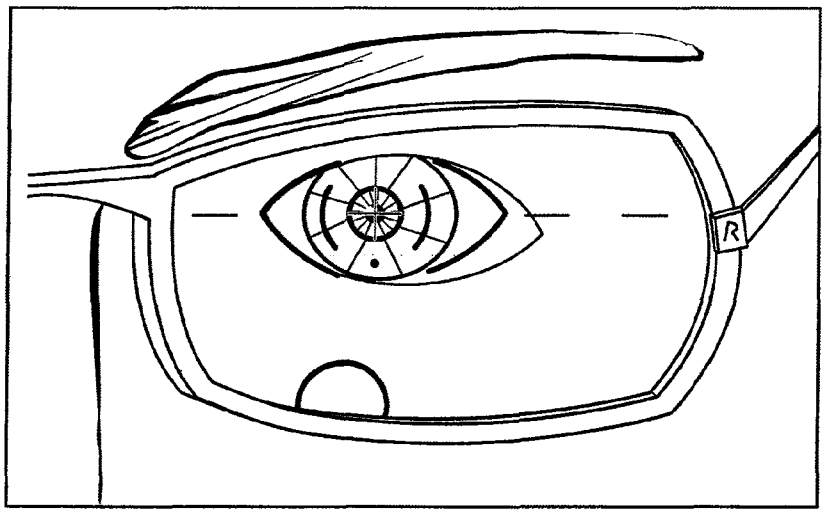

FIGS. 20a and 20b illustrate the centration of a progressive spectacle lens in front of the spectacle wearer's eyes and the corresponding position of the reference points. The spectacle lens shown in FIG. 20a is an individual spectacle lens with positions of the distance and near reference points individually determined according to a preferred method of the invention. In particular, the positions of the spectacle lens shown in FIG. 20a are specified individually depending on the frame data. The spectacle lens shown in FIG. 20b is a standard spectacle lens.

The individually calculated progressive spectacle lenses are adjusted according to reference point demands. This means, the centration and/or fitting point (or centration cross) is to be in the middle of the pupil in a habitual head and body posture in the zero direction of sight. The minimum fitting height depends on the position of the near reference point. Preferably, however, at least 2 mm remain below the near reference point in the frame. Thus, the minimum fitting height preferably is 15 mm below the centration point. If progressive lenses are adjusted differently from the centration recommendations, imaging properties may be restricted.

In the case of an erroneous centration of the spectacle lens, in particular if the centration is too low, this low centration leads to slight restrictions already in the distance zone. The differences particularly occur since the spectacle lens is not worn in the situation of wear underlying the optimization.

However, in contrast to the distance zone, considerable restrictions in a spectacle lens with lower centration can be found in the near zone. On the one hand, these restrictions result from the fact that the near zone is not present any more in the frame depending on the frame size and that the spectacle wearer looks through the progression zone in near vision, which progression zone is clearly narrower than the near zone. On the other hand, additional errors occur because the spectacle lens is not worn in the situation of wear underlying the optimization. Furthermore, with the same infraduction, the near power is not achieved and the customer has an additional accommodative effort.

An emphasis of the viewing zones can therefore correctly be created by shifting the distance and/or a near reference point, as has been described above. In addition, with a deviating principal direction of sight, e.g. in the case of particularly tall or small people, the principal viewing zones can be arranged individually such that they coincide with the respective principal direction of sight.

In the reference points, the so-called target measured values are measured as well, wherein the target measured values are indicated on the lens packet of the individual spectacle lens in addition to the ordered values. The target measured values preferably relate to the concave vertex measuring position. Tolerance considerations relate to the target measured values, not to the ordered values.

Distance Power

Figure 21A:
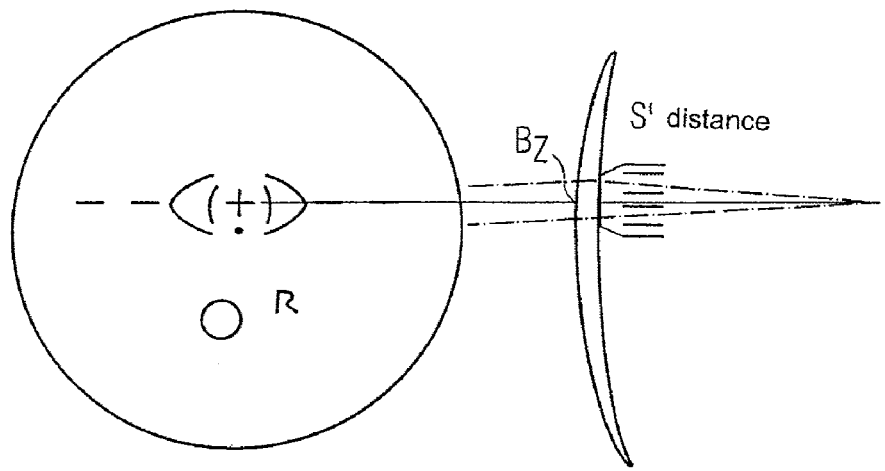
FIG. 21a-c a schematic illustration of the measurement of the powers of an individual spectacle lens.

The target measured values for sphere, cylinder and axis are checked in the distance reference point. This distance reference point is located individually in a different manner, preferably within a range of +4 to −4 mm, about the centration point. The exact position of the distance reference point can be taken from the addition engraving below the base curve and index engravings. The measurement of the distance portion power is schematically illustrated in FIG. 21a.

Prismatic Power

Figure 21B:
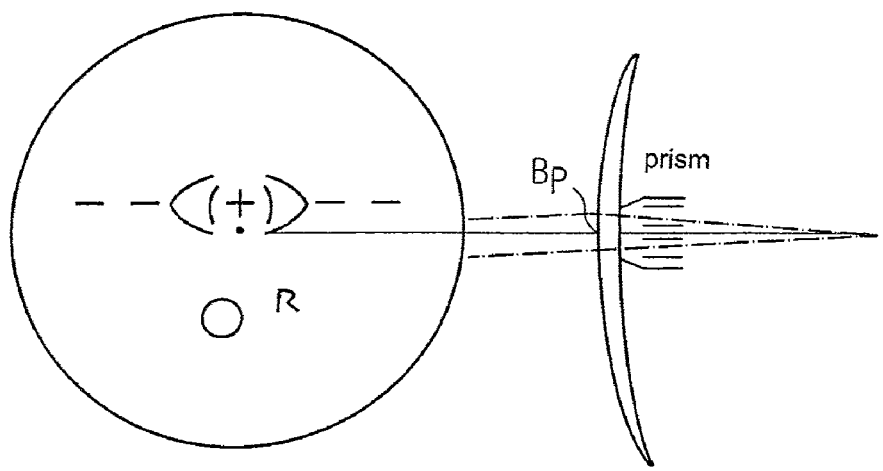

In the prism reference point, a combined power of thickness reduction prism (base position always)270° and correction prisms is measured. The measurement of the prismatic power is schematically illustrated in FIG. 21b.

Near Power

The near reference point is located individually in a different manner within a range of −13 to −20 mm below the centration point. The exact position of the near reference point can be taken from the addition engraving below the base curve and index engravings.

Figure 21C:
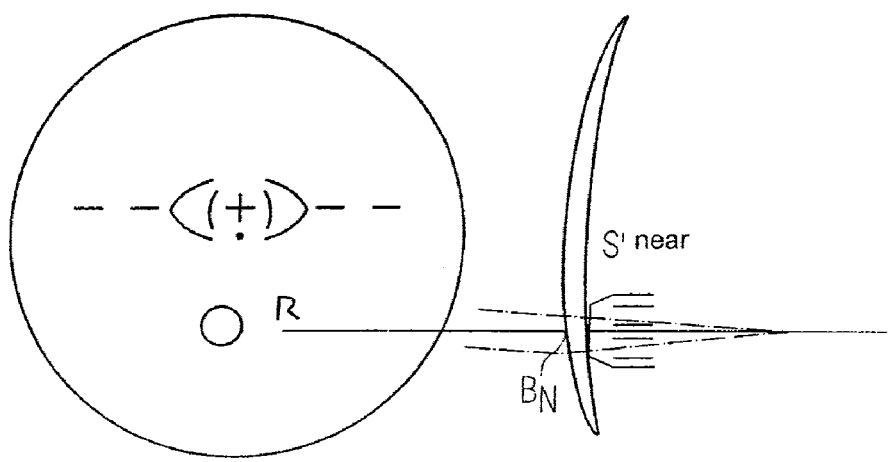

The measurement of the near power is schematically illustrated in FIG. 21c.

Addition

The target measured value of the addition corresponds to the difference of the mean power (spherical equivalent) between the distance and near reference points. However, in many cases it is easier and generally sufficient to check the correspondence of ordered and engraved additions.

The flexible spectacle lens design according to the above-described method is particularly characterized by the following advantageous characteristics:

optimum correction of visual defects by taking all refraction data (power optimization), the frame and centration data as well as PD, CVD, FI and FFA into account;

viewing zones always have the optimum size and overlap ideally, since all individual parameters and refraction data are taken into account in the optimization;

optimization
  in position of wear;
  for all refraction data;
  wavefront optimization with consideration of aberrations of higher order, such as coma and spherical aberration;
  consideration of Listing's rule;
  with Freiformtechnologie (free form technology)
highest spontaneous compatibility;

pinpoint-precise inset, can also be ordered deviating from 100% convergence (e.g. for one-eyed people);
identical viewing zones on the right/left, also in the case of anisometropia;
ordering of the refraction data for distance vision also in steps of 0.12 D;
ordering of prisms/MDM incl.;
perfect aesthetics.

Preferably, the spectacle lens design determined and calculated individually according to the customer's needs and parameters exhibits characteristic features of a balanced universal spectacle lens design, i.e. maximally large viewing zones for all distances with at the same time harmonic transitions between the central and peripheral viewing zones. Such a design or such a spectacle lens thus offers optimum vision comfort for a wide range of everyday situations (driving a car, leisure time, reading, etc.).

The invention claimed is:

1. A computer-implemented method for specifying or determining the spatial position of a distance and/or a near reference point of a progressive spectacle lens for correction of a visual defect of a spectacle wearer, comprising the following steps:
   obtaining individual data of the spectacle wearer comprising data relating to the preferences or the weighting of the distance, near and/or progression zone; and
   determining or calculating the individual vertical and/or the horizontal position of the distance and/or the near reference point depending on the obtained individual data of the spectacle wearer, wherein
   for the vertical distance $y_{BF}$ of the distance reference point from a centration or fitting point of the spectacle lens, it follows that $y_{BF}=4-4*G_F/33.33$ [mm] for $0 \leq G_F < 33$ and $y_{BF}=0-4*(G_F-33.33)/66.66$ [mm] for $33 \leq G_F \leq 100$;

and/or
   for the vertical distance $y_{BN}$ of the near reference point from the centration or fitting point, it follows that $y_{BN}=-20+2*2G_N/33$ [mm] for $0 \leq G_N < 33$ and $y_{BN}=-18+5*(G_N-33.33)/66.66$ [mm] for $33 \leq G_N \leq 100$;

wherein $G_F$ designates the weighting of the distance zone and $G_N$ designates the weighting of the near zone.

2. The method according to claim 1, wherein the vertical distance of the distance and/or the near reference point from a centration or fitting point of the spectacle lens is specified depending on the individual data of the spectacle wearer.

3. The method according to claim 1, wherein:
   the vertical height of the distance reference point, measured from the centration or fitting point of the spectacle lens, is set to a value of −4 mm below up to 4 mm above the centration or fitting point, depending on the individual data of the spectacle wearer; and/or
   the vertical height of the near reference point, measured from the centration or fitting point of the spectacle lens, is set to a value of −13 mm to −20 mm below the centration or fitting point depending on the individual data of the spectacle wearer.

4. The method according to claim 1, wherein the individual data of the spectacle wearer comprises individual parameters of the eyes of the spectacle wearer and/or of the arrangement of the spectacles in front of the eyes of the spectacle wearer.

5. The method according to claim 1, wherein the individual data of the spectacle wearer comprises data relating to
   the individual object distance for distance and/or the individual object distance for near; and/or
   the individual object distance for distance in the refraction determination and/or the individual object distance for near in the refraction determination.

6. The method according to claim 1, wherein the individual data of the spectacle wearer comprises:
   data relating to spectacles worn so far; and/or
   data relating to desired improvement of the spectacles worn so far.

7. The method according to claim 1, wherein the individual data of the spectacle wearer comprises:
   data relating to the individual main direction of sight for distance and closes-up; and/or
   data relating to the individual head and body posture; and/or
   physiological parameters of the eye of the spectacle wearer; and/or
   preferences or a weighting of the importance of the imaging properties as against the aesthetic properties of the spectacle lens.

8. The method according to claim 1, wherein the individual data of the spectacle wearer comprises data in at least two different categories of the individual data, wherein the categories of individual data correspond to different types of data, and wherein the determination of the position of the distance and/or the near reference point comprises the following steps:
   determining an ideal position of the distance reference point and/or an ideal position of the near reference point for each of the categories on the basis of individual data of the spectacle wearer in the respective category;
   calculating the position of the distance reference point and/or the position of the near reference point on the basis of the determined ideal position of the distance and/or the near reference point in the respective categories.

9. The method according to claim 8, wherein the position of the distance and/or the near reference point is calculated according to the formula:

$$y_{DF,DN} = \sum_{i=1}^{N} g_i y^i_{DF,DN}$$

$$\sum_{i=1}^{N} g_i = 1$$

wherein:
$g_i$ designates the weighting of the $i^{th}$ category;
$y_{DF,DN}^i$ designates the ideal position of the distance reference point DF and the near reference point DN, respectively, for the $i^{th}$ category; and
N designates the number of different categories.

10. The method according to claim 1, further comprising the steps of
   calculating an individual spectacle lens design exhibiting the individually specified distance and/or near reference point(s);
   visualizing the calculated, individual spectacle lens design and the spatial position of the individual distance and/or near reference point(s).

11. A computer program product stored on a non-transitory computer readable medium and adapted, when loaded and executed on a computer, to perform the method for specifying or determining the individual spatial position of a distance and/or a near reference point of a progressive spectacle lens according to claim 1.

12. A non-transitory storage medium with a computer program stored thereon, wherein the computer program product is adapted, when loaded and executed on a computer, to perform the method for specifying or determining the individual spatial position of a distance and/or a near reference point of a progressive spectacle lens according to claim 1.

13. An apparatus for determining the individual spatial position of a distance and/or a near reference point of a progressive spectacle lens, comprising:
- obtaining means for obtaining individual data of the spectacle wearer;
- calculating or optimizing means for performing a method for determining the spatial position of the distance and/or the near reference point depending on the collected individual data of the spectacle wearer according to claim 1.

14. A graphical user interface for specifying or determining and presenting the spatial position of an individual distance and/or near point of a progressive spectacle lens, comprising
- at least one individual data input portion adapted to input individual data of the spectacle wearer; and
- at least one display portion adapted to present the spatial position of the distance and/or the near reference point, wherein the spatial position of the distance and/or the near reference point is determined according to the method of claim 1, depending on the individual data of the spectacle wearer.

15. The graphical user interface according to claim 14, wherein the display portion is further adapted to present an individual spectacle lens design, wherein the individual spectacle lens design exhibits the individually set distance and/or near reference point(s).

16. The graphical user interface according to claim 14, further comprising a tuning or adaptation portion adapted to perform an adaptation of the vertical and/or the horizontal position of the distance and/or the near reference point and/or an adaptation of at least part of the individual parameters of the spectacle wearer.

17. A computer-implemented method for determining or calculating an individual spectacle lens design for a progressive spectacle lens for correction of a visual defect of a specific spectacle wearer, comprising the following steps:
- obtaining individual data of the spectacle wearer;
- determining or calculating the spatial position of a distance and/or a near reference point depending on the collected individual data of the spectacle wearer, according to the method of claim 1;
- calculating the spatial position and/or the size of a distance, a near and a progression zone of the spectacle lens design depending on the determined individual spatial position of the distance and/or the near reference point.

18. The method according to claim 17, wherein the spectacle lens design is calculated by means of the transformation of a predetermined base design, and the transformation is a function of the vertical and/or the horizontal spatial position of the specified distance and/or near reference point(s).

19. The method according to claim 17, wherein the calculation of the location and/or the size of a distance, a near and a progression zone of the spectacle lens design is further performed taking into account the collected individual data of the spectacle wearer.

20. A machine-readable computer program product adapted, when loaded and executed on a computer, to perform a method for determining or calculating an individual spectacle lens design for a progressive spectacle lens according to claim 17.

21. A storage medium with a computer program stored thereon, wherein the computer program is adapted, when loaded and executed on a computer, to perform a method for determining or calculating an individual spectacle lens design for a progressive spectacle lens according to claim 17.

22. An apparatus for determining or calculating an individual spectacle lens design for a progressive spectacle lens for correction of a visual defect of a specific spectacle wearer, comprising;
- obtaining means for obtaining individual data of the spectacle wearer;
- calculating or optimizing means for calculating the individual spatial position of a distance and/or a near reference point depending on the individual data of the spectacle wearer according to the method of claim 1;
- calculating or optimizing means for calculating the spatial position and/or the size of a distance, a near and a progression zone of the spectacle lens design depending on the calculated individual spatial position of the distance and/or near reference point(s).

23. A graphical user interface for specifying or determining and presenting an individual spectacle lens design for a progressive spectacle lens, comprising:
- at least one individual data input portion adapted to input individual data of the spectacle wearer; and
- at least one display portion adapted to present the individual spectacle lens design, wherein the individual spectacle lens design is calculated and determined according to a method of claim 17.

* * * * *

UNITED STATES PATENT AND TRADEMARK OFFICE
CERTIFICATE OF CORRECTION

PATENT NO. : 8,356,896 B2  
APPLICATION NO. : 12/524314  
DATED : January 22, 2013  
INVENTOR(S) : Esser et al.

Page 1 of 1

It is certified that error appears in the above-identified patent and that said Letters Patent is hereby corrected as shown below:

In the Specifications

In column 5, line 56 should appear as follows:

$$y_{BN} = -20 + 2*G_N/33 \text{ [mm] for } 0 \leq G_N < 33 \text{ and}$$

In column 6, line 12 should appear as follows:

$$y_{BN} = -20 + 2*G_N/33 \text{ [mm] for } 0 \leq G_N < 33 \text{ and}$$

In the Claims

In column 43, line 42 should appear as follows:

$$y_{BN} = -20 + 2*G_N/33 \text{ [mm] for } 0 \leq G_N < 33 \text{ and}$$

Signed and Sealed this  
Fourth Day of June, 2013

Teresa Stanek Rea  
*Acting Director of the United States Patent and Trademark Office*